US00RE46788E

(19) United States
(12) Reissued Patent
Koganov

(10) Patent Number: US RE46,788 E
(45) Date of Reissued Patent: Apr. 17, 2018

(54) PARTHENOLIDE FREE BIOACTIVE INGREDIENTS FROM FEVERFEW (TANACETUM PARTHENIUM) AND PROCESSES FOR THEIR PRODUCTION

(71) Applicant: ISP INVESTMENTS INC., Wilmington, DE (US)

(72) Inventor: Michael Koganov, White Plains, NY (US)

(73) Assignee: ISP INVESTMENTS LLC, Wilmington, DE (US)

(21) Appl. No.: 15/161,134

(22) Filed: May 20, 2016

Related U.S. Patent Documents

Reissue of:
(64) Patent No.: 8,728,548
Issued: May 20, 2014
Appl. No.: 12/412,126
Filed: Mar. 26, 2009

U.S. Applications:
(63) Continuation of application No. 11/677,435, filed on Feb. 21, 2007, now Pat. No. 7,537,791.

(60) Provisional application No. 60/775,257, filed on Feb. 21, 2006.

(51) Int. Cl.
*A61K 36/28* (2006.01)
*A61K 36/00* (2006.01)

(52) U.S. Cl.
CPC ..... *A61K 36/28* (2013.01)

(58) Field of Classification Search
CPC ..... A61K 36/28
See application file for complete search history.

(56) References Cited

U.S. PATENT DOCUMENTS

| | | | | |
|---|---|---|---|---|
| 6,224,875 | B1 | 5/2001 | Bombardelli et al. | |
| 6,410,062 | B1 | 6/2002 | Callaghan et al. | |
| 6,479,080 | B2 | 11/2002 | Bombardelli et al. | A61K 8/97 424/764 |
| 6,762,158 | B2 | 7/2004 | Lukenbach et al. | |
| 6,908,630 | B2 | 6/2005 | Babish et al. | |
| 7,074,747 | B1 | 7/2006 | Lukenbach et al. | |
| 7,229,650 | B2 | 6/2007 | Callaghan et al. | |
| 7,262,158 | B1 | 8/2007 | Lukenbach et al. | |
| 2002/0034489 | A1 | 3/2002 | Wiegland et al. | |
| 2002/0035046 | A1 | 3/2002 | Lukenbach et al. | |
| 2002/0182166 | A1 | 12/2002 | Martin et al. | |
| 2003/0003170 | A1 | 1/2003 | Callaghan et al. | |
| 2003/0077343 | A1 | 4/2003 | Martin et al. | |
| 2003/0175235 | A1 | 9/2003 | Koganov | |
| 2004/0105905 | A1 | 6/2004 | Callaghan et al. | |
| 2004/0167046 | A1 | 8/2004 | Lukenbach et al. | |
| 2005/0009717 | A1 | 1/2005 | Lukenbach et al. | |
| 2005/0142093 | A1 | 6/2005 | Skover et al. | |
| 2005/0148833 | A1 | 7/2005 | Skover et al. | |
| 2005/0148906 | A1 | 7/2005 | Skover et al. | |
| 2005/0148907 | A1 | 7/2005 | Skover et al. | |
| 2005/0148908 | A1 | 7/2005 | Skover et al. | |
| 2005/0148910 | A1 | 7/2005 | Skover et al. | |
| 2005/0244525 | A1 | 11/2005 | Callaghan et al. | |
| 2007/0086972 | A1 | 4/2007 | Birnbaum | |

OTHER PUBLICATIONS

Hewlett et al, "Sesquiterpene lactones from feverfew, *Tanacetum parthenium*: isolation, structural revision, activity against human blood platelet function and implications for migraine therapy" J. Chem. Soc., Perkin Trans. vol. 1, 1996, pp. 1979-1986).*

Kwok et al, "The anti-inflammatory natural product parathenolide from the medicinal herb feverfew directly binds to and inhibits I & B kinase", Chemistry & Biology 8 (2001), pp. 759-766).*

Millenia Hope Biopharma, "Millenia Hope Biopharma Announces a Major Plant Cell Culture Discovery—the Development of Parthenolide-Free Feverfew," Press Release, published online at http://milleniahope.com/more_news_articles/2006_12_05_en.htm (Dec. 5, 2006).

International Search Report and Written Opinion from PCT/US07/62498 mailed Sep. 15, 2008.

* cited by examiner

*Primary Examiner* — Bruce Campell
(74) *Attorney, Agent, or Firm* — Fisher Broyles LLP; William J. Davis

(57) ABSTRACT

The present invention relates to bioactive ingredients that include isolated bioactive fractions derived from cell juice of fresh biomass of a feverfew (Tanacetum parthenium) plant. The bioactive fractions are either free of or substantially free of α-unsaturated γ-lactones (e.g., parthenolide). Further, the bioactive fractions have anti-inflammatory and antioxidant activity. The present invention also relates to a method for isolating a bioactive fraction that is derived from cell juice of fresh biomass of a feverfew (Tanacetum parthenium) plant and that is at least substantially free of α-unsaturated γ-lactones (e.g., parthenolide). The present invention also relates to a method for preparing a stabilized cell juice serum fraction and a stabilized concentrated cell juice serum fraction that are free of α-unsaturated γ-lactones (e.g., parthenolide). The present invention also relates to a bioactive composition that includes a mixture of one or more of the isolated bioactive fractions of the present invention.

7 Claims, 7 Drawing Sheets

PARTHENOLIDE FREE BIOACTIVE INGREDIENTS FROM FEVERFEW (TANACETUM PARTHENIUM) AND PROCESSES FOR THEIR PRODUCTION

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

This application is a continuation of U.S. patent application Ser. No. 11/677,435, filed Feb. 21, 2007, which claims the benefit of U.S. Provisional Patent Application Ser. No. 60/775,257, filed Feb. 21, 2006, the disclosures of which are hereby incorporated by reference in their entirety.

FIELD OF THE INVENTION

The present invention relates to bioactive ingredients that include isolated bioactive fractions derived from cell juice of fresh biomass of a feverfew (Tanacetum parthenium) plant. The bioactive fractions are either free of or substantially free of α-unsaturated γ-lactones (e.g., parthenolide) and have anti-inflammatory and antioxidant activity. The present invention also relates to methods of making the bioactive ingredients. The present invention further relates to a bioactive composition that includes a mixture of one or more of the isolated bioactive fractions of the present invention.

BACKGROUND OF THE INVENTION

Tanacetum parthenium L. Schulz-Bip. (syn. Chrysanthemum parthenium, Leicanthemum parthenium, Matricaria parthenium, Pyrethrum parthenium) is a plant belonging to the Compositae (Asteraceae, Matricaria or daisy) family. Tanacetum parthenium is known under following common names: altamisa, amargosa, bachelor's buttons, featherfew, featherfoil, febrifuge plant, feverfew, flirtwort, grande camomille, manzanilla, matricaria, midsummer daisy, moederkruid, Santa Maria, and varadika. Of these common names, the name "feverfew" is used most frequently.

Feverfew is a short perennial plant that grows 15-80 cm tall. The stems stand straight up and are furrowed and hairy. The leaves are double divided feathery green leaves having serrate margins. The flower has white ray petals and a yellow center that is flat. The odor of the plant when bruised is strong, aromatic, and bitter. Feverfew has been grown for at least 2000 years and it is a native of the Balkan Peninsula and the Caucasus mountains. Presently, feverfew grows in Europe, North America, South America, North Africa, China, Japan, and Australia. The optimal conditions for feverfew cultivation are: well-drained soil having pH=6.0 . . . 6.7 (optimum pH=6.3); full sun or partial shade; suited to hardiness in USDA temperature zones from nine to five without protection. The best climate for feverfew is zones five and seven. With protection feverfew can be cultivated in zones three and four, although in a continental climate (e.g., Kansas, USA; Saskatchewan, Canada) feverfew sometimes is considered an annual plant.

Ancient Greeks and early Europeans used feverfew to treat fever, inflammation, and swellings, as well as to repel insects and to treat bites and stings. Within the past 20 years, feverfew has attracted considerable interest for the treatment of migraines, arthritis, and inflammatory diseases. The parts of the plant which are utilized are dried or fresh leaves and flowering aerial parts. Feverfew is used in the form of a crude herb, dried powder, fresh leaf, freeze-dried leaf capsule, dried leaf capsule, softgel capsule, tincture, infusion (e.g., tea), extracts, and ingredients of functional drinks. Apparently, the feverfew whole plant acts in a fashion similar to nonsteroidal anti-inflammatory agents. However, feverfew extracts act rather similar to cortisone (see, e.g., Feverfew. Botanical Monograph, American Journal of Natural Medicine 4(6):28-29 (1997)).

Such discrepancy and broad-spectrum activities attract attention to and the investigation of active ingredients in the plant and its derivatives. The major known active chemicals in feverfew are sesquiterpene lactones (total content ≤1.8%) and essential oils (total content ≤0.07%). The list of feverfew active compounds include the following: (i) sesquiterpene lactones (including artecanin, canin, 10-epi-canin, chrysanthemolide, chrysanthemonin, epoxyartemorin, 1β-hydroxyarbusculin, 3β-hydroxyparthenolide, 8β-hydroxyreynosin, magnoliolide, parthenolide, reynosin, santamarin, seco-tanaparthenolide A, tanaparthin, tanaphthin-1α, 4α-epoxide, tanaparthin-1β,4β-epoxide); (ii) sesquiterpenes (including camphor, β-farnesene, and germacrene); (iii) monoterpenes; (iv) flavonols (including tanetin, kaempherols, quercetagetins, apigenin, luteolin, and chrysoeritol); and (v) spiroketal enol ether polyines.

The most abundant group of these compounds is a group of α-unsaturated γ-lactones; particularly, parthenolide, which represents ~85% of α-unsaturated γ-lactones. Parthenolide, which is apparently located in oil cells on feverfew leaf surface is the most well-known and well-studied (see, e.g., Smith et al., J. Chromatogr., 627:255 (1992); and Smith, R. M., LC GC Int., (Jan. 8-15, 1996)). The α-unsaturated γ-lactones, including parthenolide, are considered to be the fundamental ingredients responsible for the biological activities of feverfew, but are also the same ingredients often responsible for allergic reactions caused by feverfew derivatives.

For example, feverfew preparations used in successful clinical trials had a parthenolide content of 0.4% to 0.66%, which exceeds the concentrations capable of initiating ulceration, exudative dermatitis, and pathological effects arising from external contact (see, e.g., Awang, D. V. C., "Feverfew," Can. Pharm. J., 122:266-270 (1989)). At the same time, about 10-18% of feverfew users have reported some usually mild and reversible adverse effects (see, e.g., Ernst et al., "The efficacy and safety of feverfew (Tanacetum parthenium L.): an update of a systematic review," Public Health Nutrition, 3(4a):509-514 (2000); Porter et al., "Feverfew in Saskatchewan," (www.agr.gov.sk.ca/DOCS/crops/special_crops/feverfew.asp?firstPick=&secondpck=&thirdpick=Production%20Information) (2004)) and parthenolide could be responsible for these adverse effects. The ability of α-unsaturated γ-lactones (including parthenolide) to trigger many allergic reactions is well documented (see, e.g., Arch. Dermatol. Forsch, 251(3):235-244 (1975); Arch. Dermatol. Forsch, 255(2):111-121 (1976); Contact Dermatitis, 38(4):207-208 (1988); Am. J. Contact Dermatol., 1:49-50 (1998-1999); Br. J. Dermatol, 132(4)543-547 (1995)).

In recent years, efforts have been directed toward preparation of feverfew extracts, which purport to be substantially-free from α-unsaturated γ-lactones and, more particularly, substantially-free from parthenolide (see, e.g., U.S. Pat. No. 6,224,875 and U.S. Pat. No. 6,479,080). It should be noted that "substantially-free from α-unsaturated γ-lactones" and "substantially-free from parthenolide" mean an extract having a weight content of α-unsaturated γ-lactone or parthenolide, respectively, below about 0.1%, more preferably below 0.1%, more preferably below about 0.09%, and most preferably below 0.07%. Because the above contents are lower than that in an average feverfew phytomass having from 0.4 to 1.8% of parthenolide (see, e.g., Marino L., "The effect of clonal micropropagation on parthenolide content in two genotypes of feverfew, Tanacetum parthenium," Agro-Farm Technologies Feverfew Report, London, Ontario (2004)), many steps of complex extraction using several organic solvents and purification, including complete evaporation of solvents and utilization of ion-exchange resin, are required to produce extracts having decreased content of α-unsaturated γ-lactones and particularly parthenolide.

The organic solvent extracts mentioned above are obtained from dried feverfew phytomass utilizing a process comprising the following steps: (a) extracting a quantity of plant material from the aerial portion of the plant with acetone, alcohols or a mixture of these solvents with water; (b) extracting the material from step (a) with a hydrocarbon solvent; (c) extracting the remaining non-hydrocarbon phase with a non-polar solvent; (d) evaporating the non-polar solvent extract and redissolving the residue in water-alcoholic solution, and then treating the redissolved residue with a strong basic resin; (e) eluting the resin with an alcohol and removing the eluted solution; (f) treating the resin with an alcoholic or water-alcoholic solution of an acid, concentrating the solution and extracting the resulting residue with a non-polar solvent; (g) evaporating the non-polar solvent from step (f) to form a residue which is added to the residue from the evaporation of the hydrocarbon extract from step (b) and to the acetonic or alcoholic phase obtained after the extraction with the non-polar solvent of step (c); and (h) evaporating the solvent and drying the remaining residue.

The preferred solvents for the various extraction steps include, but are not limited to, the following: for Step (a): acetone, methanol, ethanol or mixtures thereof with water; for Step (b): hexane, n-pentane, petroleum ether, ligroin; for Step (c): methylene chloride, chloroform, ethyl acetate, preferably methylene chloride; and for Step (f): ethyl acetate.

According to the U.S. Pat. Nos. 6,224,875 and 6,479,080, this "substantially free from parthenolide" extract has favorable pharmacological properties together with reduced risk of inducing allergic reactions. However, the above extract is isolated with sequential processing using organic solvents, which belong to four different groups, and which may have limited compatibility with many conventional components of skin care formulations. Therefore, the applicability of the above extract as an ingredient for skin care products has certain limits (e.g., not readily soluble in water).

Although the described feverfew extract is "substantially free from parthenolide," it is not truly parthenolide free material due to the allowed residual parthenolide content. Well-known high specific activities of parthenolide itself can contribute to both pharmacological properties and residual allergenicity of the extract, especially when used at high concentrations. It is important that pharmacological properties of the above extract be limited by activities of only those feverfew ingredients which are solubilized in certain solvents at certain conditions. Therefore, such extract represents only part of the active components existing in living feverfew plants. For example, freeze-dried feverfew leaves and dried leaves demonstrated significant beneficial effect when compared to a placebo, but ethanol extracts of feverfew were ineffective (see, e.g., Ernst et al., "The efficacy and safety of feverfew (Tanacetum parthenium L.): An update of a systematic review," Public Health Nutrition, 3(4a):509-514 (2000)).

With respect to comparison of specific activities found in different forms of feverfew products, it should be noted that preparation of whole dried leaves has been proven to be more effective than its extracts, and, additionally, extracts of dried and fresh feverfew have marked differences in the pharmacological potency and profiles (see, e.g., Barsby et al., "Fever-few and vascular smooth muscle: Extracts from fresh and dried plants show opposing pharmacological profiles, dependent upon sesquiterpene lactone content," Planta Medica, 59:20-25 (1993)). Thus, relative and in contrast to dried feverfew leaf extracts, the fresh leaf extracts have: (a) reduced inactivating voltage-dependent potassium current in a concentration-related manner; (b) dose-dependent inhibition of leukocyte production of tromboxane $B_2$ and leukotriene $B_4$; and (c) inhibited muscle response to triptamine, tromboxane, and reduced acetylcholine induced relaxation.

Interestingly, the strong desire to maximize the efficacy of feverfew products led recently to increased production of products containing all plant components which would be minimally impacted by the processing of the plant. Among these products are preparations of freeze-dried feverfew leaves, although such material is suitable for limited applications, and skin care is not among them.

Additionally, activities of feverfew extracts and the level of parthenolide in these extracts depend on choice of solvent(s) end explored extraction method (see, e.g., Kaplan, M., "Comparison of Supercritical Fluid and Solvent Extraction of Feverfew (Tanacetum parthenium)," Turk J. Chem, 26:473-480 (2002)). Thus, material extracted by solvent extraction and supercritical fluid extraction differ. For example, supercritical fluid $CO_2$ extracts have greater parthenolide content than chloroform extracts, and more in acetone extracts thereafter.

Composition of feverfew varies significantly, depending on the source of plant material and cultivation and harvesting conditions. Enormous variations in the amount of parthenolide have been found. For example, American-grown plants contain ≤50% of the concentration of parthenolide found in British and French-grown feverfew. Parthenolide contents were higher for dry land compared to irrigated feverfew. It was found that subjecting feverfew to a single water stress event can increase parthenolide content (Fonseca et al., "Parthenolide and abscisic acid synthesis in feverfew are associated but environmental factors affect them dissimilarly," J. Plant Physiology, 162:485-494 (2005)). Flowers contained the highest levels of parthenolide, while stems contained the least parthenolide. The parthenolide content in flowers increased and the content of the stems and leaves decreased as harvest was delayed. Feverfew harvested during the afternoon contained significantly more parthenolide than plants harvested in the morning and exposure of feverfew to ultraviolet (UV) light resulted in significantly decreased parthenolide content. It should be noted that wide variation in amount of parthenolide in feverfew derivatives could be the essential result of interaction of two major factors: cultivation conditions and processing methods. Unfortunately, U.S. Pat. Nos. 6,224,875 and 6,479,080 do not provide any information relating to reproducibility of the "substantially free from parthenolide" feverfew extract. However, as described above, large variability of raw material may have significant impact on extract properties.

Thus, there are many genetic, geographic, climatic, and technological factors, which lead to poor reproducibility and less than fully optimal quality of conventional feverfew products and extracts (see, e.g., Hepinstall et al., "Parthenolide content and bioactivity of feverfew (Tanacetum parthenium (L.) Schultz-Bip.). Estimation of commercial and authenticated feverfew products," J. Pharm. Pharmacol., 44:391-395 (1992); Draves, A. H. and S. E. Walker, "Parthenolide Content of Canadian Commerical Feverfew Preparations Label Claims are Misleading in Most Cases," Canadian Pharm J, 136(10):23-30 (December 2003/January 2004)) and these factors create serious problems for broad utilization of feverfew derivatives in herbal medicine and skin care.

Therefore, there is a need for a method of production of highly reproducible and parthenolide free feverfew derivatives having a broad spectrum of desirable biological activities, which are not limited by only those activities which have affinity to certain solvents, i.e., which are not otherwise subject to the limitations of conventional chemical extraction.

SUMMARY OF THE INVENTION

The present invention relates to bioactive ingredients that include isolated bioactive fractions derived from cell juice of fresh biomass of a feverfew (Tanacetum parthenium) plant. The bioactive fractions are either free of or substantially free of α-unsaturated γ-lactones (e.g., parthenolide). Further, the bioactive fractions have anti-inflammatory and antioxidant activity.

The present invention also relates to a method for isolating bioactive fractions that are derived from cell juice of fresh biomass of a feverfew (Tanacetum parthenium) plant and that are either free of or substantially free of α-unsaturated γ-lactones (e.g., parthenolide). This method involves providing fresh biomass of a feverfew (Tanacetum parthenium) plant. The fresh biomass is processed under conditions effective to yield a cell juice supernatant and a membrane fraction. The cell juice supernatant is treated under conditions effective to yield a first cell juice serum supernatant and a cytoplasm fraction precipitate. The cytoplasm fraction precipitate is then isolated as a bioactive fraction that is at least substantially free of α-unsaturated γ-lactones. The present invention also relates to a bioactive ingredient that includes the cytoplasm fraction precipitate produced by this method, and that has anti-inflammatory and antioxidant activity.

The present invention also relates to a method for preparing a stabilized cell juice serum fraction that is a bioactive fraction that is derived from cell juice of fresh biomass of a feverfew (Tanacetum parthenium) plant and that is free of α-unsaturated γ-lactones (e.g., parthenolide). This method involves clarifying the first cell juice serum supernatant under conditions effective to yield a second cell juice serum supernatant. A stabilizing agent is mixed with the second cell juice serum supernatant under conditions effective to yield a stabilized cell juice serum fraction. The stabilized cell juice serum fraction is a bioactive fraction that is free of α-unsaturated γ-lactones. The present invention also relates to a bioactive ingredient that includes the stabilized cell juice serum fraction produced by this method, and that has anti-inflammatory and antioxidant activity.

The present invention also relates to a method for preparing a stabilized concentrated cell juice serum fraction that is a bioactive fraction that is derived from cell juice of fresh biomass of a feverfew (Tanacetum parthenium) plant and that is free of α-unsaturated γ-lactones (e.g., parthenolide). This method involves concentrating the stabilized cell juice serum fraction under conditions effective to yield a concentrated cell juice serum supernatant. A stabilizing agent is mixed with the concentrated cell juice serum supernatant under conditions effective to yield a stabilized concentrated cell juice serum fraction. The stabilized concentrated cell juice serum fraction is a bioactive fraction that is free of α-unsaturated γ-lactones. The present invention also relates to a bioactive ingredient that includes the stabilized concentrated cell juice serum fraction produced by this method, and that has anti-inflammatory and antioxidant activity.

The present invention further relates to a bioactive composition that includes a mixture of one or more of the isolated bioactive fractions of the present invention.

The present invention is useful in that it provides a means for making highly reproducible and parthenolide-free or substantially parthenolide-free feverfew derivatives having a broad spectrum of desirable biological activities (e.g., anti-inflammatory and antioxidant activities). One advantage of the present invention over the prior art is that the method of the present invention does not require the use of harsh organic solvents to isolate the bioactive fractions of the present invention. The bioactive ingredients of the present invention are useful as active ingredients in various topical and oral applications to mammals (including humans). These formulations can be used for inhibiting inflammatory activity in the skin tissue and for protecting the skin tissue from ultraviolet light-induced damage. The bioactive ingredients of the present invention can also be used for normalizing skin disorders in skin tissue of a mammal.

DETAILED DESCRIPTION OF THE INVENTION

Figure 1:
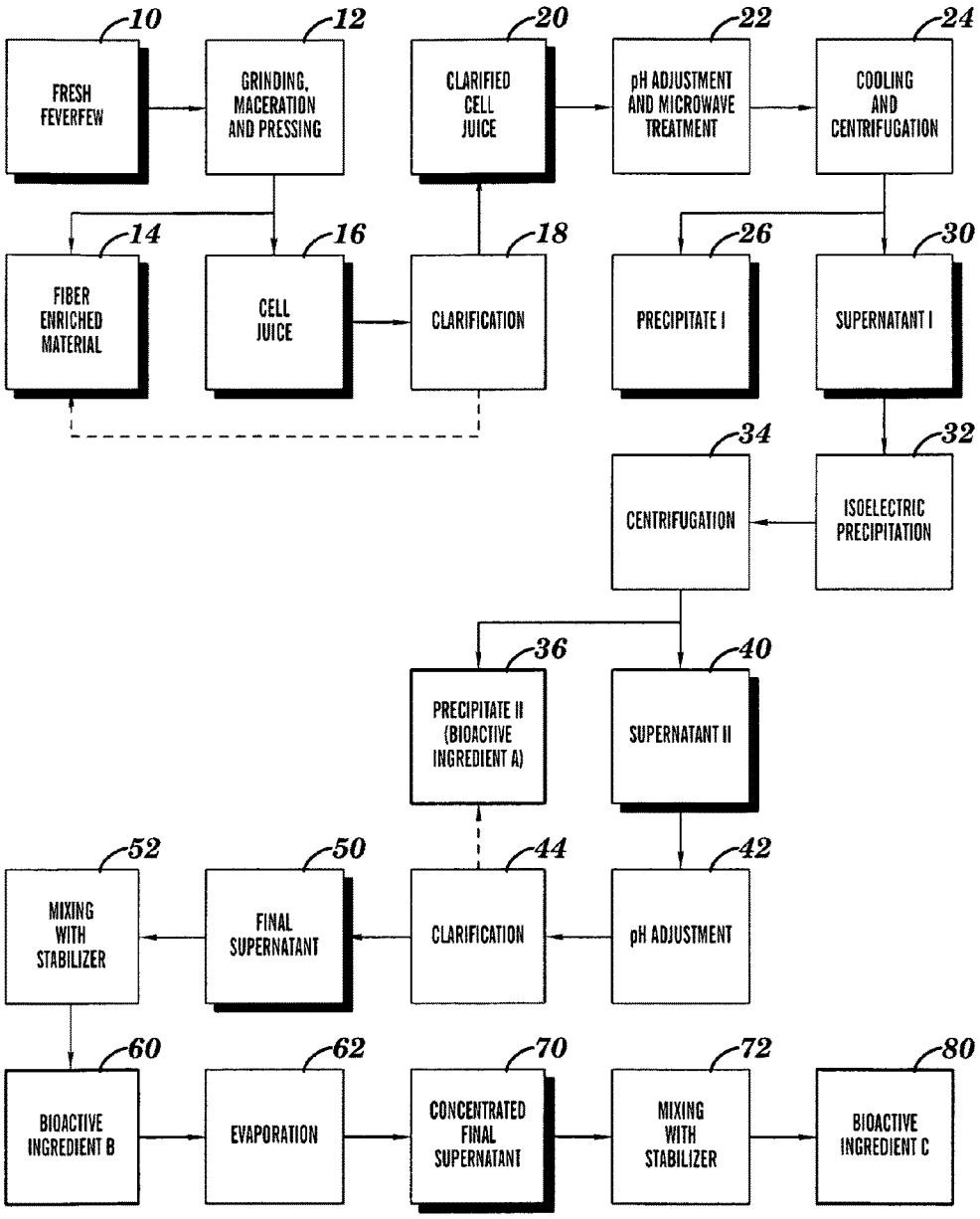
FIG. 1 is a schematic drawing demonstrating one embodiment of the process for preparing the bioactive ingredients of the present invention.

The present invention relates to bioactive ingredients that include isolated bioactive fractions derived from cell juice of fresh biomass of a feverfew (Tanacetum parthenium) plant. The bioactive fractions are either free of or substantially free of α-unsaturated γ-lactones, and more particularly are either free of or substantially free of parthenolide. As used herein, the term "bioactive fraction" and "bioactive ingredient" can be used interchangeably. In view of the present specification, the ordinarily skilled artisan will know when such interchangeable usage of the terms is appropriate. The bioactive ingredients of the present invention have favorable activities, including, without limitation, anti-inflammatory and antioxidant activities.

As used herein, the term "feverfew" is the common name for the "Tanacetum parthenium" plant.

As used herein, the terms "substantially free of α-unsaturated γ-lactones" and "substantially free of parthenolide" refer to a feverfew bioactive ingredient or bioactive fraction having a weight content of α-unsaturated γ-lactones or parthenolide, respectively, equal to or less than about 0.01%, but still within the detectable limit for α-unsaturated γ-lactones or parthenolide using standard high pressure liquid chromatography ("HPLC") analytical assays well known in the art. As used herein, all percentages used to refer to the weight content or concentration of α-unsaturated γ-lactones or parthenolide in the bioactive ingredients/bioactive fractions of the present invention, unless otherwise noted, refer to percent by weight (commonly abbreviated by the symbol "wt %" or the phrase "weight percent").

As used herein, the terms "free of α-unsaturated γ-lactones" and "free of parthenolide" refer to a feverfew bioactive ingredient or bioactive fraction having a weight content of α-unsaturated γ-lactones or parthenolide, respectively, that is below the detectable limit for α-unsaturated γ-lactones or parthenolide using standard HPLC analytical assays well known in the art. In one embodiment, the bioactive ingredients/bioactive fractions that are free of parthenolide have a weight content of parthenolide that is less than 0.00007 wt %. Those of ordinary skill in the art would recognize the bioactive ingredients/bioactive fractions of the present invention that are "free of α-unsaturated γ-lactones" or "free of parthenolide" to be characterized as being "completely free of α-unsaturated γ-lactones" or "completely free of parthenolide," respectively.

A suitable method for detecting parthenolide amount is further described in Example 6 (infra). Briefly, such a method for detecting parthenolide involves detection at 225 nm, where parthenolide concentrations are determined using a multipoint calibration curve developed with six parthenolide standards (Sigma-Aldrich Corporation, St. Louis, Mo.) ranging from 30 μg of parthenolide/gram of sample to 900 μg of parthenolide/gram of sample. In one embodiment, the detection limit of parthenolide under these conditions is 0.7 μg of parthenolide/mL of sample (i.e., 0.00007%). About 30 μg of parthenolide/gram of sample (i.e., 0.003%) can be quantitated using these set of conditions.

In one embodiment, the bioactive ingredient of the present invention corresponds to a "cytoplasm fraction precipitate" as defined herein. In reference to the schematic of the process described in FIG. 1, this embodiment includes a category of bioactive ingredient to which "Precipitate II 36" would belong. Further, as described in the Examples section (infra), this embodiment includes a category of bioactive ingredient to which "Bioactive Ingredient A" would belong. As demonstrated in the Examples, one embodiment of Bioactive Ingredient A of the present invention was shown to contain about 0.01 wt % of parthenolide, and therefore would qualify as being substantially free of parthenolide. In another embodiment, the bioactive ingredient corresponding to the "cytoplasm fraction precipitate" can have an HPLC profile corresponding to the profile shown in FIG. 5, or the like.

In another embodiment, the bioactive ingredient of the present invention corresponds to a "stabilized cell juice serum fraction" as defined herein. In reference to the Examples section (infra) and the schematic of the process described in FIG. 1, this embodiment includes a category of bioactive ingredient to which "Bioactive Ingredient B" and "Bioactive Ingredient B 60" would belong. As demonstrated in the Examples, one embodiment of Bioactive Ingredient B of the present invention was shown to contain below 0.00007 wt % of parthenolide, and therefore is defined as being free of parthenolide. In other words, the amount of parthenolide in this embodiment of bioactive ingredient was found to be below the detection limit of the analytical procedure used to detect parthenolide (see Example 6, "Method for Determination of Parthenolide Content"). In another embodiment, the bioactive ingredient corresponding to the "stabilized cell juice serum fraction" can have an HPLC profile corresponding to the profile shown in FIG. 6, or the like. The bioactive ingredient of this embodiment is readily soluble in water.

In still another embodiment, the bioactive ingredient of the present invention corresponds to a "stabilized concentrated cell juice serum fraction" as defined herein. In reference to the Examples section (infra) and the schematic of the process described in FIG. 1, this embodiment includes a category of bioactive ingredient to which "Bioactive Ingredient C" and "Bioactive Ingredient C 80" would belong. As demonstrated in the Examples, one embodiment of Bioactive Ingredient C of the present invention was shown to contain below 0.00007 wt % of parthenolide, and therefore is defined as being free of parthenolide. In other words, the amount of parthenolide in this embodiment of bioactive ingredient was found to be below the detection limit of the analytical procedure used to detect parthenolide (see Example 6, infra). In another embodiment, the bioactive ingredient corresponding to the "stabilized concentrated cell juice serum fraction" can have an HPLC profile corresponding to the profile shown in FIG. 7, or the like. The bioactive ingredient of this embodiment is readily soluble in water.

The bioactive fraction of the present invention has anti-inflammatory and antioxidant activity.

With respect to anti-inflammatory activity, such activity can be determined using an elastase inhibition assay (see, e.g., Example 6, "Method for Determination of Elastase Inhibitory Activity"). In one embodiment, the bioactive ingredient of the present invention has an anti-inflammatory activity expressed in $IC_{50}$ values ranging from about 0.1% (v/v) to about 2.0% (v/v), particularly from about 0.3% (v/v) to about 1.7% (v/v). As used herein to define anti-inflammatory activity, the term "$IC_{50}$ value" refers to the concentration of bioactive ingredient required to decrease the speed of elastase enzymatic reaction by 50%. As shown in Tables 4, 7, 10, and 13, anti-inflammatory activity (in $IC_{50}$ values) of the identified bioactive ingredients can be expressed in terms of volume (e.g., microliters, μL), and then recalculated in terms of a volume per volume (v/v) concentration. The anti-inflammatory data shown in Tables 4, 7, 10, and 13 was based on a volume of 3.0 mL of reaction mixture.

With respect to antioxidant activity, such activity can be determined using a superoxide scavenging assay (see, e.g., Example 6, "Method for Determination of Superoxide Scavenging Activity"). In one embodiment, the bioactive ingredient of the present invention has an antioxidant activity expressed in $IC_{50}$ values ranging from about 0.007% (v/v) and about 1.0% (v/v), particularly from about 0.067% (v/v) to about 0.27% (v/v). As used herein to define antioxidant activity, the term "$IC_{50}$ value" refers to the concentration of bioactive ingredient required to decrease the speed of cytochrome c reduction by 50%. As shown in Tables 4, 7, 10, and 13, antioxidant activity (in $IC_{50}$ values) of the identified bioactive ingredients can be expressed in terms of volume (e.g., microliters, μL), and then recalculated in terms of a volume per volume (v/v) concentration. The antioxidant shown in Tables 4, 7, 10, and 13 was based on a volume of 3.0 mL of reaction mixture.

In one embodiment, the bioactive ingredient can be used for topical applications with or without a stabilizing agent. Suitable stabilizing agents are those conventionally used in the art, and can include, without limitation, an emulsifier, a preservative, an antioxidant, a polymer matrix, and mixtures thereof.

As used herein, "topical application" generally refers to techniques relating to directly laying on or spreading the bioactive ingredients of the present invention or formulations containing these bioactive ingredients onto the outer skin using, e.g., by use of the hands or an applicator such as a wipe.

The bioactive ingredients (and formulations containing them) are "cosmetically acceptable." As used herein, the term "cosmetically acceptable" refers to bioactive ingredients, formulations, cosmetically active agents, or inert ingredients that are suitable for use in contact with mammalian tissues (e.g., the skin of humans) without undue toxicity, incompatibility, instability, irritation, allergic response, and the like, commensurate with a reasonable benefit/risk ratio.

The bioactive ingredients (and formulations containing them) are useful for topical and oral application to humans, and can be applied in a "safe and effective amount." As used herein, the term "safe and effective amount" refers to an amount of bioactive ingredient or formulation sufficient to significantly induce a positive modification in the condition to be regulated or treated, but low enough to avoid serious side effects. The safe and effective amount of the bioactive ingredient or formulation containing the bioactive ingredient will vary with the particular condition being treated, the age and physical condition of the end user, the severity of the condition being treated/prevented, the duration of the treatment, the nature of concurrent therapy, the specific bioactive ingredient or formulation employed, the particular cosmetically-acceptable topical carrier utilized, and like factors.

The formulations containing the bioactive ingredients of the present invention may be prepared using methodology that is well known by an artisan of ordinary skill.

The present invention also relates to a method for isolating bioactive fractions that are derived from cell juice of fresh biomass of a feverfew (Tanacetum parthenium) plant and that are either free of or substantially free of α-unsaturated γ-lactones (e.g., parthenolide). This method involves providing fresh biomass of a feverfew (Tanacetum parthenium) plant. Suitable fresh biomass can include any part of the feverfew plant, including, for example, its leaves, flowers, shoots, stems, and roots. The fresh biomass is processed under conditions effective to yield a cell juice supernatant and a membrane fraction. The cell juice supernatant is treated under conditions effective to yield a first cell juice serum supernatant and a cytoplasm fraction precipitate. In one embodiment, the "cytoplasm fraction precipitate" corresponds to Bioactive Ingredient A (see FIG. 1 and the Examples section). The cytoplasm fraction precipitate is then isolated as a bioactive fraction that is substantially free of α-unsaturated γ-lactones, particularly substantially free of parthenolide.

One embodiment for processing the fresh biomass under conditions effective to yield the cell juice supernatant and the membrane fraction, is as follows: (i) the fresh biomass is separated into a cell juice component and a fiber enriched material; (ii) the cell juice component is clarified to yield a clarified cell juice component; and (iii) the clarified cell juice component is separated into the cell juice supernatant and the membrane fraction.

The present invention also relates to a method for preparing a stabilized cell juice serum fraction that is a bioactive fraction that is derived from cell juice of fresh biomass of a feverfew (Tanacetum parthenium) plant and that is free of α-unsaturated γ-lactones (e.g., parthenolide). This method involves clarifying the first cell juice serum supernatant (described above) under conditions effective to yield a second cell juice serum supernatant. A stabilizing agent (suitable examples of which are described herein) is mixed with the second cell juice serum supernatant under conditions effective to yield a stabilized cell juice serum fraction. The stabilized cell juice serum fraction is a bioactive fraction that is free of α-unsaturated γ-lactones, and particularly free of parthenolide. In one embodiment, the "stabilized cell juice serum fraction" corresponds to Bioactive Ingredient B (see FIG. 1 and the Examples section).

The present invention also relates to a method for preparing a stabilized concentrated cell juice serum fraction that is a bioactive fraction that is derived from cell juice of fresh biomass of a feverfew (Tanacetum parthenium) plant and that is free of α-unsaturated γ-lactones, particularly free of parthenolide. This method involves concentrating the stabilized cell juice serum fraction (described above) under conditions effective to yield a concentrated cell juice serum supernatant. A stabilizing agent (suitable examples of which are described herein) is mixed with the concentrated cell juice serum supernatant under conditions effective to yield a stabilized concentrated cell juice serum fraction. The stabilized concentrated cell juice serum fraction is a bioactive fraction that is free of α-unsaturated γ-lactones, and particularly free of parthenolide. In one embodiment, the "stabilized concentrated cell juice serum fraction" corresponds to Bioactive Ingredient C (see FIG. 1 and the Examples section).

The present invention also relates to the bioactive ingredients made from the above described methods, including, for example, bioactive ingredients that contain (i) the cytoplasm fraction precipitate produced by the method of the present invention; (ii) the stabilized cell juice serum fraction produced by the method of the present invention; and (iii) the stabilized concentrated cell juice serum fraction produced by the method of the present invention. These bioactive ingredients have anti-inflammatory and antioxidant activity.

By way of example, one embodiment of the overall process for preparing the bioactive ingredients of the present invention (e.g., Bioactive Ingredient A, Bioactive Ingredient B, and Bioactive Ingredient C) is schematically shown in FIG. 1. Details of the steps of this process are further described below in this Detailed Description and in the Examples.

As depicted in FIG. 1, fresh feverfew 10 (i.e., fresh biomass of feverfew) is provided. In one embodiment, the step described in this paragraph corresponds to the step defined as "providing fresh biomass of a feverfew (Tanacetum parthenium) plant." Fresh feverfew 10 is subjected to grinding, maceration, and pressing 12 under conditions effective to separate fresh feverfew 10 into cell juice 16 and fiber enriched material 14. Cell juice 16 is then subjected to clarification 18 under conditions effective to yield clarified cell juice 20. Clarified cell juice 20 is subjected to pH adjustment/microwave treatment 22 and then cooling/centrifugation 24 under conditions effective to yield Precipitate I 26 (membrane fraction) and Supernatant I 30 (cell juice supernatant). This step is effective in partitioning a substantial amount of the α-unsaturated γ-lactones (particularly parthenolide) into Precipitate I 26, which also includes much of the membrane material found in clarified cell juice 20. As used to describe the amount of α-unsaturated γ-lactones (particularly parthenolide) contained in Precipitate I 26, the term "substantial amount" refers to a content of α-unsaturated γ-lactones (particularly parthenolide) that exceeds 0.01 wt % and/or that is comparable to the content of α-unsaturated γ-lactones (particularly parthenolide) in fresh feverfew. Thus, Supernatant I 30 that is produced by this step includes cell juice that is at least substantially free of α-unsaturated γ-lactones, and particularly at least substantially free of parthenolide. In one embodiment, the step described in this paragraph corresponds to the step defined as "processing the fresh biomass under conditions effective to yield a cell juice supernatant and a membrane fraction."

Supernatant I 30 is subjected to isoelectric precipitation 32 and thereafter centrifugation 34 under conditions effective to yield Supernatant II 40 (e.g., first cell juice serum supernatant) and Precipitate II 36 (e.g., cytoplasm fraction precipitate). In one embodiment, the step described in this paragraph corresponds to the step defined as "treating the cell juice supernatant under conditions effective to yield a first cell juice serum supernatant and a cytoplasm fraction precipitate."

Precipitate II 36 is then isolated. In one embodiment, Precipitate II 36 corresponds to Bioactive Ingredient A, and is substantially free of α-unsaturated γ-lactones, and particularly substantially free of parthenolide. In one embodiment, the step described in this paragraph corresponds to the step defined as "isolating the cytoplasm fraction precipitate." Precipitate II 36 (Bioactive Ingredient A) also has various favorable bioactivities, including, but not limited to, anti-inflammatory and antioxidant activity.

Supernatant II 40 (e.g., first cell juice serum supernatant) is subjected to pH adjustment 42 and thereafter subjected to clarification 44 under conditions effective to Final Supernatant 50 (also referred to in one embodiment the "second cell juice serum supernatant"). Final Supernatant 50 is then subjected to mixing with stabilizer 52 under conditions effective to yield Bioactive Ingredient B 60 (also referred to in one embodiment as the "stabilized cell juice serum fraction"). Bioactive Ingredient B 60 is substantially free of α-unsaturated γ-lactones, and particularly substantially free of parthenolide. In one embodiment, the collective steps described in this paragraph correspond to the steps defined as (i) "clarifying the first cell juice serum supernatant under conditions effective to yield a second cell juice serum supernatant"; and (ii) "mixing a stabilizing agent with the second cell juice serum supernatant under conditions effective to yield a stabilized cell juice serum fraction." Bioactive Ingredient B 60 also has various favorable bioactivities, including, but not limited to, anti-inflammatory and antioxidant activity.

Bioactive Ingredient B 60 is subjected to evaporation 62 under conditions effective to concentrate Bioactive Ingredient B 60 to yield Concentrated Final Supernatant 70 (also referred to in one embodiment as the "concentrated cell juice serum supernatant"). In one embodiment, this step corresponds to the step defined as "concentrating the stabilized cell juice serum fraction under conditions effective to yield a concentrated cell juice serum supernatant." Concentrated Final Supernatant 70 is then subjected to mixing with stabilizer 72 under conditions effective to yield Bioactive Ingredient C 80 (also referred to in one embodiment as the "stabilized concentrated cell juice serum fraction"). In one embodiment, this step corresponds to the step of "mixing a stabilizing agent with the concentrated cell juice serum supernatant under conditions effective to yield a stabilized concentrated cell juice serum fraction." Bioactive Ingredient C 80 is free of α-unsaturated γ-lactones, and particularly free of parthenolide. Bioactive Ingredient C 80 also has various favorable bioactivities, including, but not limited to, anti-inflammatory and antioxidant activity. The bioactive ingredients of the present invention include all of the cell juice derived bioactive fractions depicted in FIG. 1, namely, the bioactive fractions represented by the following: (i) Supernatant I 30; (ii) Supernatant II 40; (iii) Precipitate II 36 (Bioactive Ingredient A); (iv) Final Supernatant 50; (v) Bioactive Ingredient B 60; (vi) Concentrated Final Supernatant 70; and (vii) Bioactive Ingredient C 80. The bioactive fractions represented by those listed in this paragraph are each either free of or substantially free of α-unsaturated γ-lactones, and particularly free of or substantially free of parthenolide. Further, the bioactive fractions represented by those listed in this paragraph each have anti-inflammatory and antioxidant activity.

The present invention also relates to bioactive compositions that include a mixture of one or more isolated bioactive fractions derived from cell juice of fresh biomass of a feverfew (Tanacetum parthenium) plant. Suitable bioactive fractions can include, without limitation, any of the bioactive fractions of the present invention. In particular, the suitable bioactive fractions are each either free of or substantially free of α-unsaturated γ-lactones, and particularly free of or substantially free of parthenolide. Further, the suitable bioactive fractions have anti-inflammatory and antioxidant activity. In one embodiment, the bioactive composition can include, without limitation, a mixture of one or more of the bioactive fractions/bioactive ingredients described in FIG. 1, namely, Supernatant I 30, Supernatant II 40, Precipitate II 36 (Bioactive Ingredient A), Final Supernatant 50, Bioactive Ingredient B 60, Concentrated Final Supernatant 70, and/or Bioactive Ingredient C 80. The bioactive compositions of the present invention are either free of or substantially free of α-unsaturated γ-lactones, and particularly free of or substantially free of parthenolide. The bioactive compositions also have anti-inflammatory and antioxidant activity. In one embodiment, the bioactive composition includes a stabilizing agent. Methods of combining the one or more bioactive fractions of the present invention to yield the bioactive compositions of the present invention are well known in the art, and are contemplated as part of the present invention.

The bioactive ingredients and bioactive compositions of the present invention can be used in various methods for mammals (including humans). Further, due to the low concentration of parthenolide (or the absence of parthenolide altogether) in the bioactive ingredients, methods of using the bioactive ingredients can include applications that are safe not only for adults, but also for children of all ages (including, without limitation infants, toddlers, and juveniles, and teens).

Further embodiments of the bioactive ingredients of the present invention are summarized below.

In one embodiment, the bioactive ingredients are derived from fresh aerial biomass of feverfew at any stage of growth, including, but not limited by, the stages providing maximum yield: from the early stage of full bloom (10% flowers) to full bloom (100% flowers) stage.

In one embodiment, the bioactive ingredients can be derived from fresh phytomass, which can be collected from plants cultivated in the first and/or the following years of growth.

In another embodiment, the bioactive ingredients can be derived from fresh phytomass, which is cultivated in the fields and/or in the greenhouses and/or in phytotron and/or in tissue cultures and/or in calluses.

Suitable bioactive ingredients can include, without limitation, any components of a plant cell, which have no binding and/or affinity to α-unsaturated γ-lactones, particularly to parthenolide.

In one embodiment, the suitable bioactive ingredients can include, without limitation, any components of a plant cell which have anti-inflammatory properties and have no binding and/or affinity to α-unsaturated γ-lactones, particularly to parthenolide.

In another embodiment, the suitable bioactive ingredients can include, without limitation, any components of the plant cell which have inhibitory activity against proteinases released during the inflammatory response in human tissues. The above proteinases can include, but are not limited to, human neutrophil elastase, which is one of the more destructive enzymes among proteinases. Because elastase can degrade multiple components of the extracellular matrix of human tissues, inhibitors of elastase are considered as important bioactives capable of reducing tissue damage associated with a broad variety of inflammatory conditions. Although purified parthenolide itself demonstrates certain anti-elastase activity, it was unexpectedly found that the substantially parthenolide free and completely parthenolide free bioactive ingredients of the present invention have higher elastase inhibitory activity, which is about two orders of magnitude higher than the activity of purified parthenolide.

It was found that the bioactive ingredients of the present invention, which have no binding and/or affinity to α-unsaturated γ-lactones, particularly to parthenolide, have an anti-elastase activity which is superior to the activity of pure parthenolide.

In one embodiment, suitable bioactive ingredients of the present invention can include, without limitation, any components of plant cells which have elastase inhibitory properties and have no binding and/or affinity to α-unsaturated γ-lactones, particularly to parthenolide.

In one embodiment, the suitable bioactive ingredients of the present invention can include, without limitation, any components of plant cell which have antioxidant properties and have no binding and/or affinity to α-unsaturated γ-lactones, particularly to parthenolide.

The present invention also relates to bioactive ingredients, which are (i) substantially or completely free of α-unsaturated γ-lactones, particularly of parthenolide, and have (ii) anti-inflammatory, and (iii) anti-oxidant properties desirable for skin care including topical and oral applications.

In one embodiment, the suitable bioactive ingredients can include, without limitation, any components of plant cell which have anti-inflammatory and antioxidant properties and have no binding and/or affinity to α-unsaturated γ-lactones, particularly to parthenolide.

In one embodiment, the suitable bioactive ingredients can include, without limitation, any components of plant cell which have elastase inhibitory and antioxidant properties and have no binding and/or affinity to α-unsaturated γ-lactones, particularly to parthenolide.

The present invention also relates to a method for isolating from cell juice of fresh biomass of a feverfew (Tanacetum parthenium) the bioactive ingredients for skin care, which are (i) substantially or completely free of α-unsaturated γ-lactones, particularly of parthenolide, and which possess (ii) anti-inflammatory, and/or (iii) antioxidant properties.

The present invention also relates to a method for isolating from cell juice obtained from fresh biomass of a feverfew (Tanacetum parthenium) the bioactive ingredients for skin care, which are (i) substantially or completely free of α-unsaturated γ-lactones, particularly of parthenolide, and which possess (ii) elastase inhibitory, and/or (iii) antioxidant properties.

In one embodiment, the method of the present invention involves fresh biomass of a feverfew (Tanacetum parthenium). The fresh biomass is then separated into cell juice and a fiber enriched material.

It should be noted that, depending on conditions of feverfew cultivation, year of growth, and particular harvest, the dry matter content in plant biomass can significantly vary and it may impact the consistency of cell juice properties and thus reproducibility of cell juice derived bioactive ingredients. The present invention allows for the standardization of cell juice properties to improve reproducibility of bioactive ingredients.

In one embodiment, the standardization of cell juice properties is improved by exploring uniform conditions for feverfew cultivation and harvesting.

In another embodiment, the proper adjustment of regimes of fresh feverfews grinding, maceration, and pressing allows cell juice to be obtained having a dry matter content which is varied in a relatively narrow range (for example, 7.0±1.6%). For example, if dry matter content in plant biomass is decreased due to environmental impact, the fine grinding of feverfew and higher pressure allows the dry matter content in cell juice to be increased and its reproducibility improved. If dry matter content in plant biomass in increased, course grinding and lower pressure can be utilized.

In another embodiment, standardization of cell juice is provided without undesirable increase of its temperature.

It should be pointed out that the above adjustments address the reproducibility of cell juice, and may not necessarily decrease the content of α-unsaturated γ-lactones, particularly of parthenolide, in the cell juice when compared on a dry matter basis with fresh feverfew or with fiber enriched material. Although parthenolide is apparently concentrated in oil cells, which are localized on feverfew leaf surface (see, e.g., Smith et al., J. Chromatogr., 627:255 (1992); and Smith, R. M., LC GC Int., Jan. 8-15, 1996, which are hereby incorporated by reference in their entirety), it was unexpectedly found that parthenolide is not predominately concentrated in fiber enriched material but rather distributed between the above material and cell juice.

In one embodiment, the fiber enriched material is dried or can be stored at freezer conditions.

In another embodiment, parthenolide containing fiber enriched material is utilized for conventional applications of feverfew derivatives that are commonly used in the art.

Fresh feverfew cell juice is a relatively stable colloidal dispersion having a dark green color. This color is contributed to chloroplasts and their fragments, which are dispersed in continuous cell juice phase having brown color and enriched with other components of cytoplasm. It was unexpectedly found that in this colloidal dispersion α-unsaturated γ-lactones, particularly parthenolide, have strong binding and/or affinity with chloroplasts and their fragments.

In one embodiment, the removal of chloroplasts and their fragments from cell juice allowed for obtaining a continuous cell juice phase, which is substantially free of α-unsaturated γ-lactones, particularly of parthenolide. The removal of these undesirable compounds from cell juice can be achieved by different treatments including, but not limited to, pH adjustment, heat treatment, microwave radiation, centrifugation, microfiltration, ultrafiltration and combinations thereof.

In one embodiment, fresh feverfew cell juice is separated into a dark green paste precipitate consisting of chloroplasts and a brown liquid supernatant, which is substantially free of α-unsaturated γ-lactones, particularly of parthenolide.

In another embodiment, the above separation can be achieved by medium-speed or high-speed centrifugation (≥15,000 g). As a result, all chloroplasts and their fragments can be concentrated in a precipitate (thereafter Precipitate I), and the isolated supernatant (thereafter Supernatant I) remains completely free from chlorophyll. As a result, almost all parthenolide pool of this colloidal dispersion is concentrated in Precipitate I and thus Supernatant I has ≤20 times lower parthenolide content (for example, 0.03%) compared to initial cell juice, i.e., the above Supernatant I of the present invention should be categorized as substantially free of α-unsaturated γ-lactones, particularly of parthenolide. (The supernatant of the present invention has significantly lower residual parthenolide content compared to preferred embodiment level in feverfew extract as described in the U.S. Pat. Nos. 6,224,875 and 6,479,080, which are hereby incorporated by reference in their entirety).

Medium and high-speed centrifugations have certain technical and/or economical limitations especially on a large industrial scale. In one embodiment, fresh feverfew cell juice is treated to decrease stability of chloroplasts and their fragments, and then destabilized cell juice is effectively separated using low speed centrifugation (≤3,000 g). The criterion of effective separation is the absence of characteristic chlorophyll maximum in spectra of Supernatant I.

The present invention includes several treatments to decrease phase stability of feverfew cell juice initiating coagulation of chloroplasts and their fragments. In one embodiment, stability of cell juice can be decreased using freeze-thaw treatment (≥1 cycle), heat treatment (≥40° C.), pH adjustment (pH=3.0 . . . 4.0), and/or combinations thereof. The above treatments of feverfew cell juice with subsequent low-speed centrifugation allow for obtaining cell juice Supernatant I containing 6.5-7.3% dry matter and only 0.01-0.035% parthenolide. The separation of chloroplasts and their fragments allow for production of Supernatant I, which is substantially free of α-unsaturated γ-lactones, particularly of parthenolide.

In one embodiment, the content of dry matter in Supernatant I can be increased without significant changes in its parthenolide content. Thus, prior to separation, the cell juice is treated with intensive stirring (for example, using rotostat) or homogenization (for example, using polytron homogenizer) or with ultrasonic treatment or with microwave radiation, and/or combinations thereof to enable part of chloroplast components having no strong binding and/or no affinity to of α-unsaturated γ-lactones, particularly of parthenolide, to move into continuous (soluble) phase of dispersion. The above process allows further increase of dry matter content in Supernatant I without elevation of the content of α-unsaturated γ-lactones, particularly of parthenolide. As a result, separated chloroplasts and their fragments may capture in Precipitate I only 15-20% of total cell juice dry matter and thus 80-85% of total dry matter remains in enriched cell juice Supernatant I.

In one embodiment, the Precipitate I enriched with α-unsaturated γ-lactones, particularly of parthenolide, is stored at temperature ≤−20° C. In another embodiment, the Precipitate I is dried (for example, using lyophylizer or spray dryer or fluid bed drier). In another embodiment, the Precipitate I is preserved (for example, with 0.75% Glucono Delta Lactone and 0.25% Sodium Erythrobate or with 1.0% Phenonip) and then stored at refrigerated conditions.

In one embodiment, parthenolide containing Precipitate I is utilized for conventional applications of feverfew derivatives that are commonly used in the art.

Although Supernatant I is substantially free of α-unsaturated γ-lactones, particularly of parthenolide, the present invention allows quantitative removal of these undesirable components from supernatant without decreasing its desirable bioactivities.

In one embodiment, the quantitative removal of residual α-unsaturated γ-lactones, particularly of parthenolide, is achieved by utilizing different additional treatments of Supernatant I. These treatments include, but are not limited by, following: (i) increase pH of Supernatant I (6.0≤pH≤10.0), which initiates isoelectric precipitation of components having affinity to α-unsaturated γ-lactones, particularly of parthenolide; (ii) separation of precipitated components using centrifugation and/or filtration to enable concentration of the above components in Precipitate II; (iii) pH adjustment of obtained Supernatant II to the initial pH value of cell juice; and (iv) additional clarification of Supernatant II using centrifugation and/or filtration or micro-filtration (≤0.22 μm pore size) or ultrafiltration (molecular weight cutoff ≥10,000 Dalton) to enable obtaining of Final Supernatant. The above resulted in isolation of Final Supernatant, which is completely free of α-unsaturated γ-lactones, particularly of parthenolide, but contains all desirable bioactivities.

In one embodiment, the resultant Precipitate II is dried (for example, using lyophylizer or spray dryer or fluid bed drier). In another embodiment, the Precipitate II is stored at freezing conditions.

In one embodiment, the stabilization of Final Supernatant is completed by adding preservatives as was previously described in U.S. Patent Application Publication No. 2003/0175235, which is hereby incorporated by reference in its entirety, and incubating the mixture until complete solubilization was achieved. The preservatives used included the following: 0.1% Potassium Sorbate, 0.1% Sodium Benzoate, 0.1% Sodium Methyl Paraben, 0.1% Sodium Metabisulfite, and 0.1% Citric Acid 75%. The preserved Final Supernatant is stored at ambient conditions.

In one embodiment, Final Supernatant is concentrated using evaporation or dialysis or electro-dialysis or reverse osmosis or combination thereof. Evaporation was selected as preferable technique because it enables the integrity of the bioactive ingredients to be preserved without undesirable removal of any components other than water.

In another embodiment, Concentrated Final Supernatant, which is an unstable opalescent dark brown color suspension capable of spontaneously forming light beige color precipitate, is mixed with stabilizer, including, but not limited by, ≥5.0% Glycerin or Pentylene Glycol (1,2-Pentanediol or 1,2-Dihydroxypentane).

The present invention further relates to isolated bioactive ingredients, which are substantially free or completely free of α-unsaturated γ-lactones, particularly of parthenolide, and have desirable bioactivities: Precipitate II (Bioactive Ingredient A), Final Supernatant (Bioactive Ingredient B), and Concentrated Final Supernatant (Bioactive Ingredient C).

In one embodiment, the isolated bioactive ingredients are combined with a stabilizing agent. Particular suitable stabilizing agents can include, without limitation, a preservative, an antioxidant, and/or mixtures thereof.

In another embodiment, the isolated bioactive ingredients are concentrated and then stabilized for further utilization in skin care for oral and topical applications.

The bioactive ingredients of the present invention can further be included in delivery systems that are commonly used in the art.

All bioactive ingredients of the present invention can be used as solutions, suspensions, dispersions, pastes, or dried powders incorporated into skin care products, including topical and oral applications.

EXAMPLES

The following examples are intended to illustrate particular embodiments of the present invention, but are by no means intended to limit the scope of the present invention.

Example 1

Preparation of Bioactive Ingredients Derived from Fresh Feverfew

Below is a description of relevant aspects of one embodiment of the method of the present invention.

Figure 2:
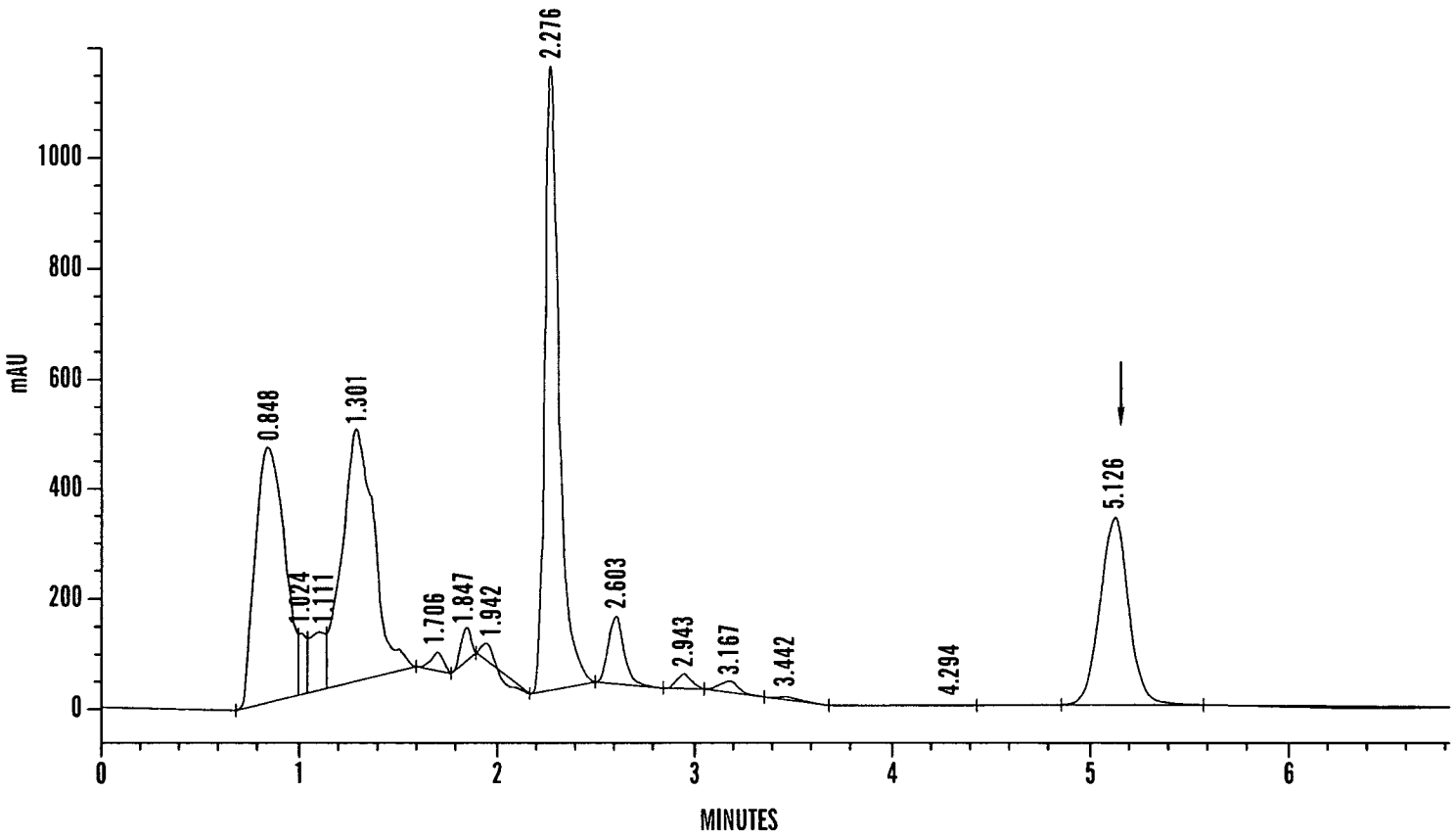
FIG. 2 is a high pressure liquid chromatography ("HPLC") chromatogram of feverfew fresh biomass used in one embodiment of the process of the present invention. The down arrow shows the peak of parthenolide.

Sufficient amount of fresh feverfew (Tanacetum parthenium) aerial parts were harvested at full bloom stage of growth to yield approximately 100 kg of dry matter. The level of dry matter in the fresh feverfew was measured to be 23.77%, requiring harvesting of approximately 420.7 kg of fresh plant phytomass to yield 100 kg of dry matter. HPLC chromatogram of utilized feverfew is presented in FIG. 2.

Care was taken to preserve the inherent moisture content of fresh feverfew and to avoid wilting due to moisture loss. The harvesting was conducted in such a manner as to avoid or minimize chopping, mashing, and crushing of the collected fresh feverfew. All steps were completed in the shortest possible period of time. This was done to minimize exposure of the fresh feverfew to sun, high temperature, and other negative environmental factors.

Then the washing step was performed to remove soil particles and other debris from the plants prior to further processing. It was accomplished by washing the harvested feverfew for ≤5 minutes in ≤1 kg/cm$^2$ water pressure. The residual water wash did not contain any green or brown pigments, indicating proper water pressure and washing duration. The excess water was removed from the washed phytomass.

The washed feverfew underwent grinding, maceration, and pressing to obtain the intracellular content (i.e. the cell juice) and to separate it from fiber-enriched material. A hammer mill (Model VS 35, Vincent Corporation, Tampa, Fla.) having 5 HP engine and set of screens was used to grind the biomass to yield feverfew tissue particles of suitably small size in a shortest amount of time and without significant increase of biomass temperature. The hammer mill was set to produce the maximum size of macerated plant particles of ≤2.0 centimeters during ≤10 seconds of treatment. The biomass temperature was increased only ≤5° C.

A horizontal continuous screw press (Compact Press CP-6, Vincent Corporation, Tampa, Fla.), equipped with cone supported by compressed air, was immediately used to obtain cell juice from macerated feverfew. The pressure on the cone was maintained at a level of ≥20 kg/cm$^2$, with a screw speed of 12 rpm and only a temperature increase of ≤5° C.

This treatment yielded fiber enriched material and cell juice. The residual small fiber particles were additionally removed from cell juice using for its clarification semi-automatic continuous flow centrifuge (Model 12-413V, AML Industries, Inc., Hatboro, Pa.) at ≤3,000 rpm and retention time ≥30 sec. The precipitate was collected and combined with fiber enriched material obtained after pressing of feverfew.

Figure 3:
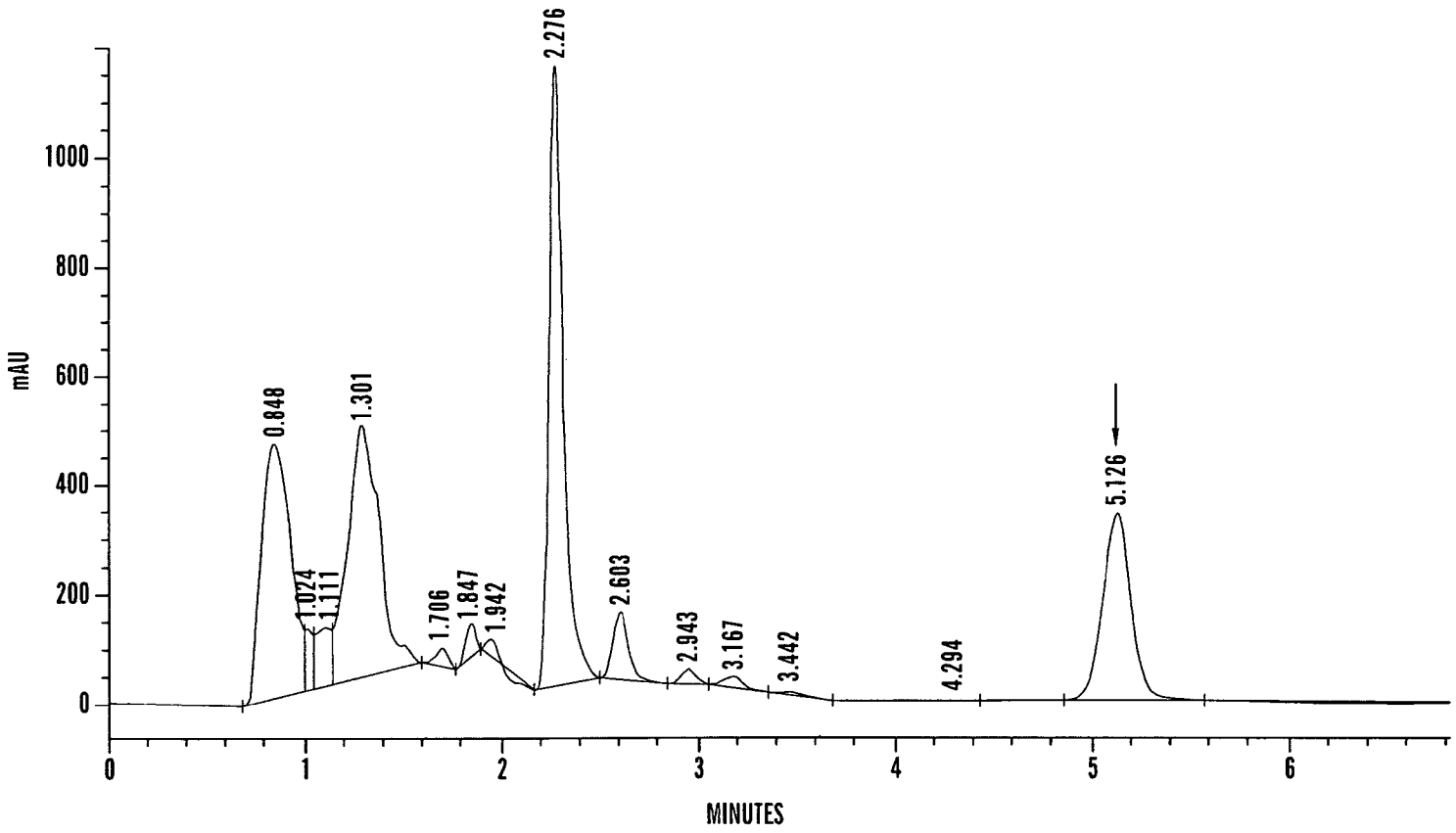
FIG. 3 is an HPLC chromatogram of fiber enriched material isolated by one embodiment of the process of the present invention. The down arrow shows the peak of parthenolide.

Processes described above allowed for the production of 217.2 kg of feverfew cell juice having dry matter level 8.20% and 203.5 kg of fiber enriched material having dry matter level 40.39%. HPLC chromatogram of fiber enriched material is presented in FIG. 3.

The cell juice was then subjected to various treatments including pH adjustment, microwave radiation and separation. The pH of fresh feverfew cell juice (initial pH=5.3) was adjusted using a titration method utilizing 3.6 liter of 5.0 N Hydrochloric Acid (HCl) to decrease the pH of the cell juice to 3.5. Then the adjusted cell juice was immediately exposed to microwave radiation using specially designed continuous flow system having 2.45 GHz frequency and 3,200 Watt output power (Microwave Research & Applications, Inc., Laurel, Md.). This system was equipped with constant speed stirrer BDC 1850 (Caframo Ltd., Wiarton, Ontario, Canada) and a temperature control probe. This treatment continued until the temperature of the cell juice in microwave chamber reached 92° C. and then the treated cell juice was immediately pumped through a continuous flow device which was connected with a 1 HP recirculating chiller (Model 6106 P, Polyscience Corporation, Niles, Ill.).

After the temperature of treated cell juice was decreased to ≤30° C., the material was separated using a continuous flow centrifuge CEPA LE (Carl Padberg Zentrifugenbau GmbH, Germany) at 15,000 rpm and retention time ≥30 sec. The separation of 220.8 kg of treated cell juice yielded a 19.2 kg of dark green color paste precipitate (thereafter Precipitate I) having dry matter content 26.2% and a 201.6 kg of brown color slightly opalescent liquid supernatant (thereafter Supernatant I) having dry matter content 6.34%.

Figure 4:
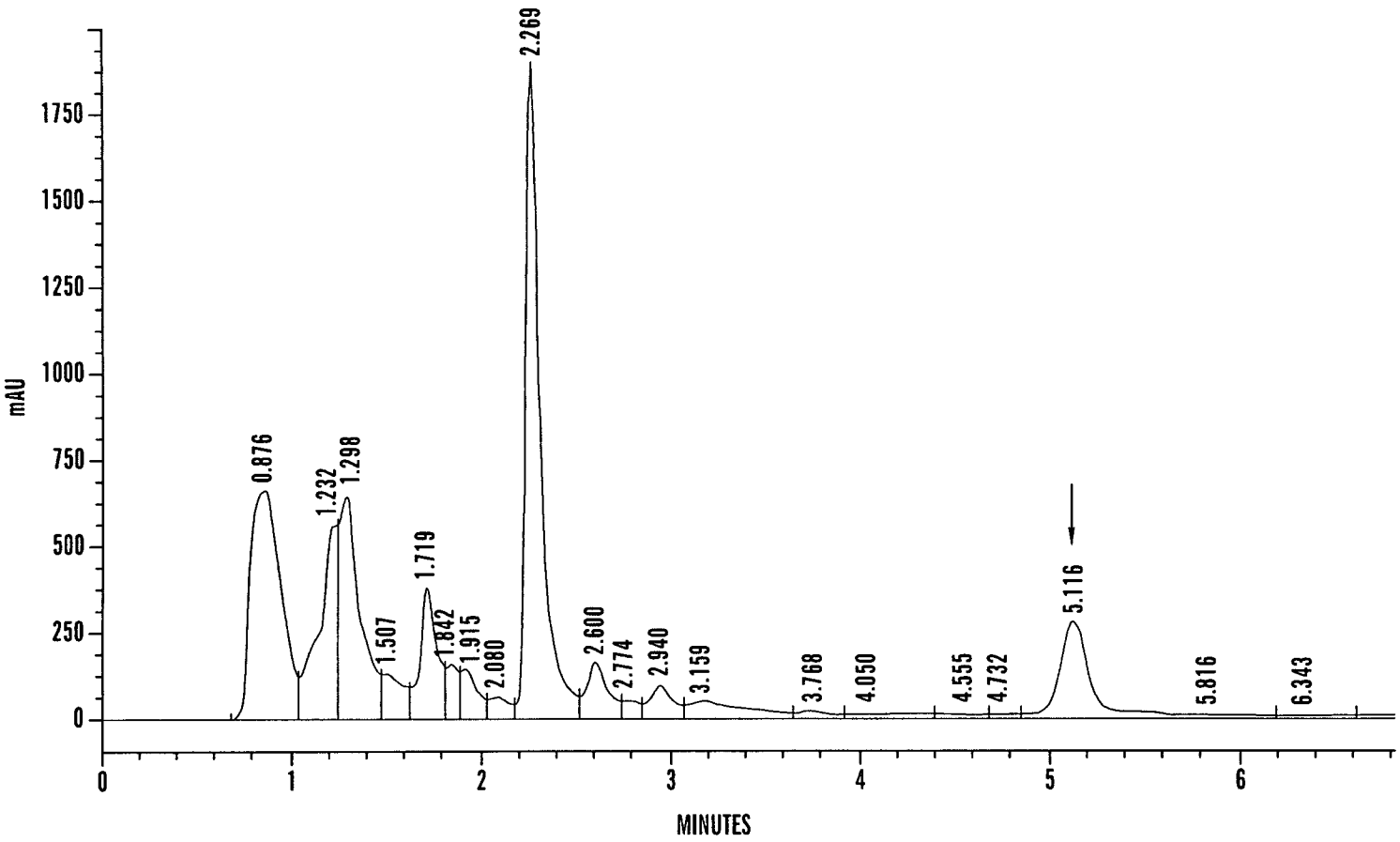
FIG. 4 is an HPLC chromatogram of Precipitate I isolated by one embodiment of the process of the present invention. The down arrow shows the peak of parthenolide.

HPLC chromatogram of Precipitate I is presented in FIG. 4. It is noteworthy that the HPLC profile shown in FIG. 4 for Precipitate I is significantly different from the HPLC profile of the feverfew extract described in U.S. Pat. No. 6,479,080 (see FIG. 1). Therefore, the composition of Precipitate I and of the feverfew extract described in U.S. Pat. No. 6,479,080 are significantly different.

Supernatant I was then subjected to further treatment including pH adjustments and separations. The first pH adjustment was induced using a titration method utilizing 1.07 liter 50% Potassium Hydroxide (KOH) to increase pH of cell juice Supernatant I from 3.5 to 9.0. This treatment resulted in developed opalescence and darker color of material which was immediately clarified using continuous flow centrifuge CEPA LE (Carl Padberg Zentrifugenbau GmbH, Germany) at 15,000 rpm and retention time ≥30 sec. The above separation yielded 0.55 kg dark beige color paste precipitate (thereafter Precipitate II) having dry matter content 38.2% and 202.12 kg brown color slightly opalescent supernatant (thereafter Supernatant II) having dry matter content 6.22%.

Figure 5:
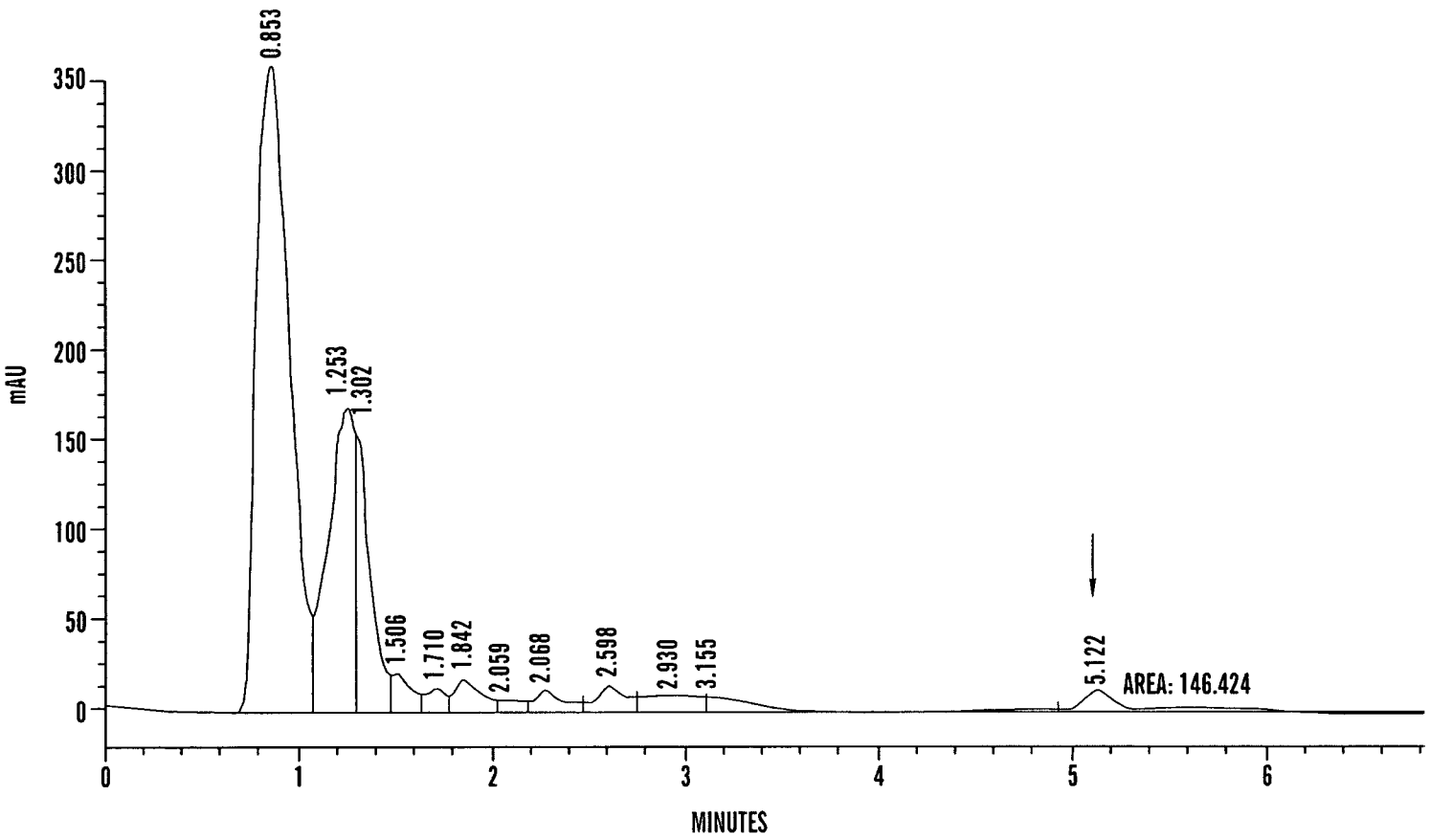
FIG. 5 is an HPLC chromatogram of Precipitate II (Bioactive Ingredient A) isolated by one embodiment of the process of the present invention. The down arrow shows the peak of parthenolide.

HPLC chromatogram of Precipitate II is presented in FIG. 5. It is noteworthy that the HPLC profile shown in FIG. 5 for Precipitate II is significantly different from the HPLC profile of the feverfew extract described in U.S. Pat. No. 6,479,080 (see FIG. 1). Therefore, the composition of Precipitate II and of the feverfew extract described in U.S. Pat. No. 6,479,080 are significantly different.

The Precipitate II contained 0.01% parthenolide as determined by HPLC analysis represents Bioactive Ingredient A, which is substantially free of α-unsaturated γlactones, particularly of parthenolide.

The Supernatant II was subjected to isoelectric titration utilizing 5.0 N Hydrochloric Acid (HCl) to return the pH value to pH=3.5 as existed in initial Supernatant I. Such treatment led to increased slight opalescence of material but it was effectively clarified using continuous flow centrifuge CEPA LE (Carl Padberg Zentrifugenbau GmbH, Germany) at 15,000 rpm and retention time ≥60 sec. The clarified material (thereafter Final Supernatant) contained <0.00007% parthenolide as determined by HPLC analysis and, therefore, in accordance with the detection limits, the above Final Supernatant should be considered free of parthenolide, and particularly completely free of parthenolide.

Stabilization of the Final Supernatant was achieved by adding preservatives and antioxidant and incubating the mixture until complete solubilization was achieved. The preservatives and antioxidant used included the following: 0.1% potassium sorbate, 0.1% sodium benzoate, 0.1% sodium methyl paraben, and 0.2% sodium metabisulfite. This preparation resulted in the production of 201.6 kg of Bioactive Ingredient B containing 6.8% dry matter. The yield of Bioactive Ingredient B from 100 kg Dry Matter of initial feverfew biomass is approximately 12.5 kg Dry Matter.

Figure 6:
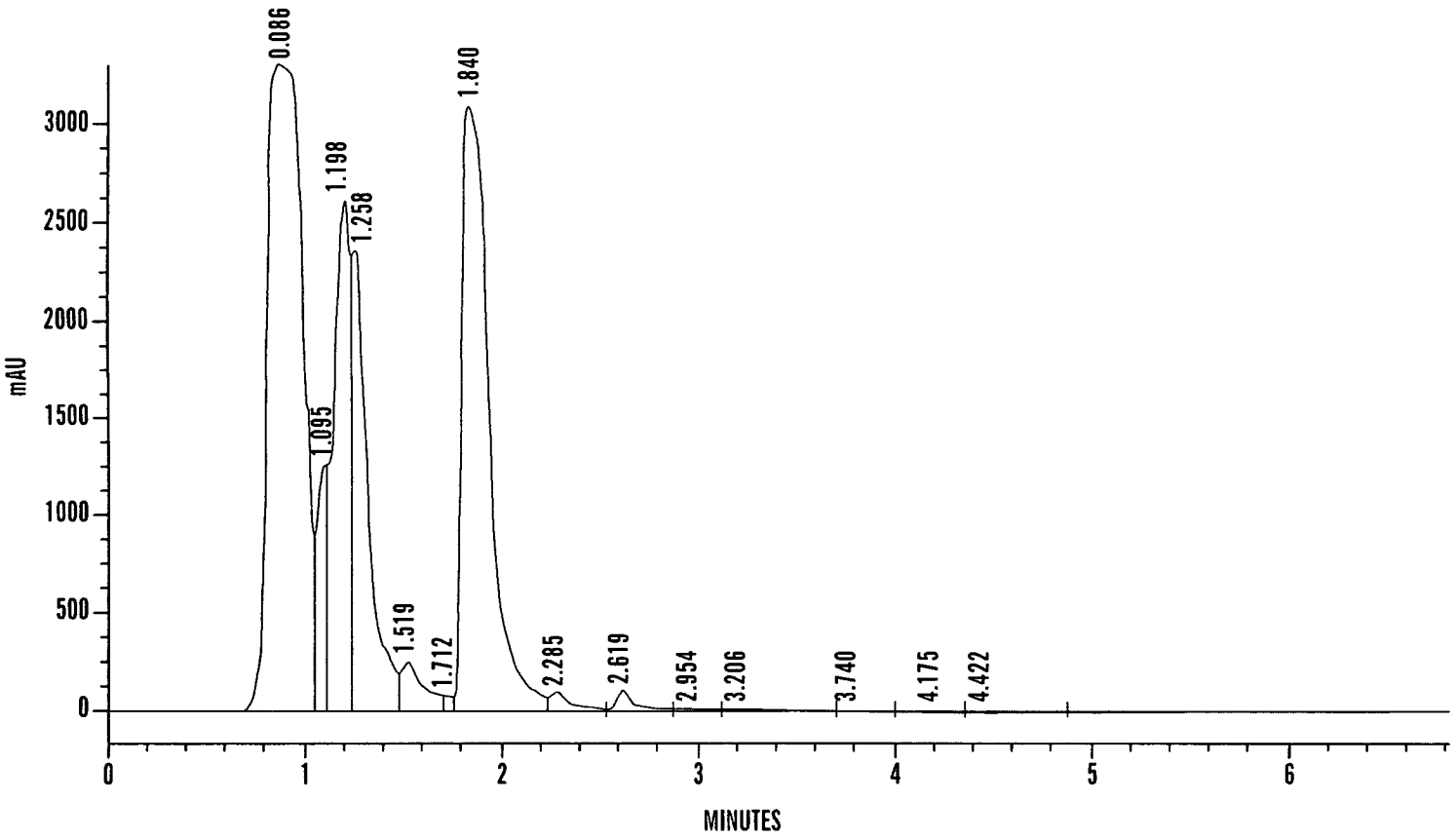
FIG. 6 is an HPLC chromatogram of Final Supernatant (Bioactive Ingredient B) isolated by one embodiment of the process of the present invention.

HPLC chromatogram of Bioactive Ingredient B is presented in FIG. 6. It is noteworthy that the HPLC profile shown in FIG. 6 for Bioactive Ingredient B is significantly different from the HPLC profile of the feverfew extract described in U.S. Pat. No. 6,479,080 (see FIG. 1). Therefore, the composition of Bioactive Ingredient B and of the feverfew extract described in U.S. Pat. No. 6,479,080 are significantly different.

The Bioactive Ingredient B was also concentrated utilizing Rapid Vap vacuum evaporation system (Labconco, Kanzas City, Mo.) equipped with eight 0.6 Liter tubes, 2.550 Liter liquid trap and diaphragm vacuum pump (Model 2018B-01, Welch Rietsche Thomas, Skokie, Ill.). Using operating pressure=100 mBar, temperature=60° C. and vortex speed=40%, Bioactive Ingredient B was concentrated in 90 minutes cycles to produce total 63.16 Liter (or 70.11 kg) of concentrated material having dry matter content 19.89%. Then 5.0% (w/w) Pentylene Glycol was added to concentrated material and after moderate mixing during ≥60 sec transparent dark-brown resulted liquid: Bioactive Ingredient C was produced. The Bioactive Ingredient C contained <0.00007% parthenolide as determined by HPLC analysis and, therefore, in accordance with the detection limits, the above Bioactive Ingredient C should be considered free of parthenolide, and particularly completely free of parthenolide.

Figure 7:
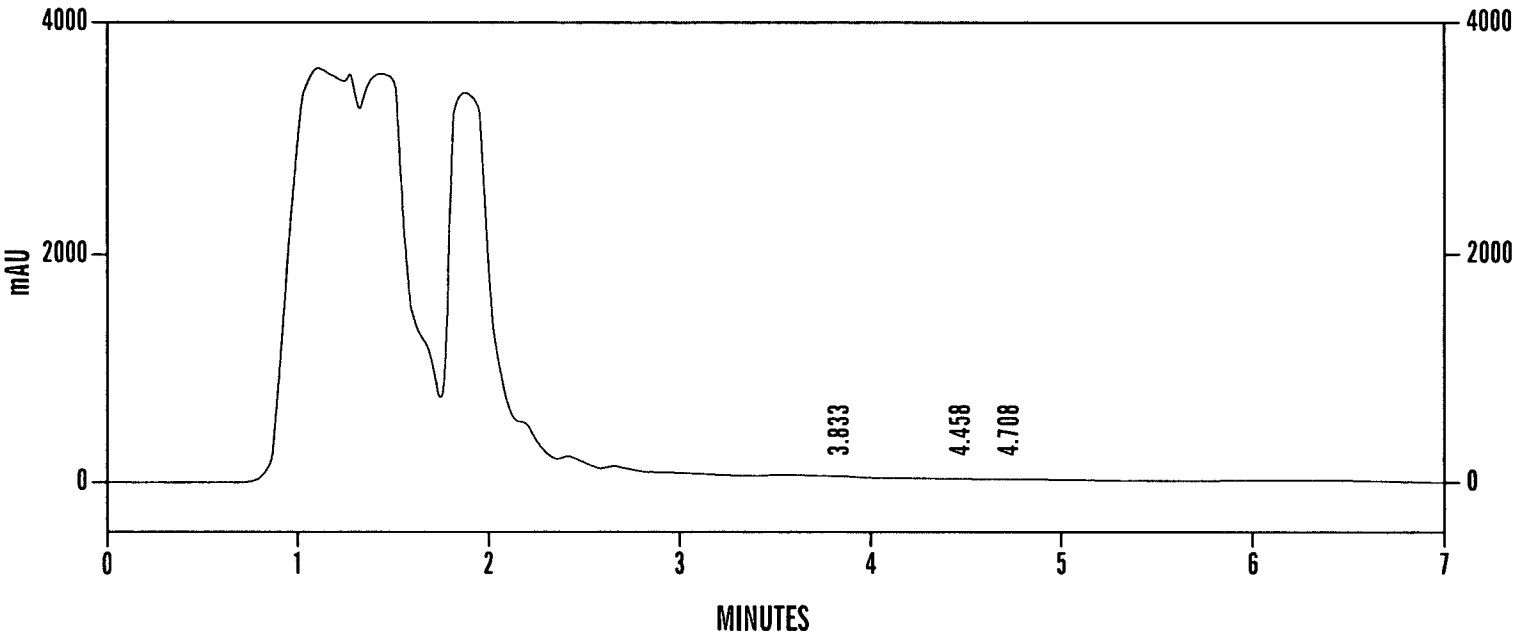
FIG. 7 is an HPLC chromatogram of Concentrated Final Supernatant (Bioactive Ingredient C) isolated by one embodiment of the process of the present invention.

HPLC chromatogram of Bioactive Ingredient C is presented in FIG. 7. It is noteworthy that the HPLC profile shown in FIG. 7 for Bioactive Ingredient C is significantly different from the HPLC profile of the feverfew extract described in U.S. Pat. No. 6,479,080 (see FIG. 1). Therefore, the composition of Bioactive Ingredient C and of the feverfew extract described in U.S. Pat. No. 6,479,080 are significantly different.

Example 2

Characteristics and Properties of Bioactive Ingredient B

Bioactive Ingredient B was prepared according to the process described above in Example 1. Analyses of Bioactive Ingredient B were conducted to determine its various physico-chemical, chemical, and microbial characteristics.

The selected physico-chemical and chemical characteristics of Bioactive Ingredient B are presented below in Table 1.

TABLE 1

Physico-Chemical & Chemical Characteristics of Bioactive Ingredient B

| Parameter | Results |
|---|---|
| Appearance | Yellow-Brown Liquid |
| Odor | Characteristic |
| Color (Gardner Scale) | 11.5 |
| Dry Matter, % | 6.6 |
| Specific Gravity, g/cm$^3$ | 1.030 |
| Refractive Index, nD | 1.3112 |
| pH | 4.1 |
| UV Maximum, nm | 269 |
| Parthenolide, % | <0.00007 |

Bioactive Ingredient B is readily soluble in water in any proportion.

Table 2 below describes the microbial characteristics of Bioactive Ingredient B. This data demonstrates that Bioactive Ingredient B satisfies skin care industry requirements regarding total plate count, mold and yeast count, and absence of pathogens.

TABLE 2

Microbial Characteristics of Bioactive Ingredient B

| Parameter | Results |
|---|---|
| Total Plate Count, CFU*/g | <100 |
| Mold &Yeast, CFU*/g | <10 |
| Escherichia coli | Negative |
| Salmonella sp. | Negative |
| Staphylococcus aureus | Negative |
| Pseudomonas sp. | Negative |

*Colony Forming Units

The results of antimicrobial effectiveness testing presented in Table 3 below indicates, that Bioactive Ingredient B has an effective system of preservatives.

TABLE 3

Results of Antimicrobial Effectiveness Testing of Bioactive Ingredient B

| | Colony Forming Units, CFU/g | | | | |
|---|---|---|---|---|---|
| Microorganism | Initial Count | Day 7 | Day 14 | Day 21 | Day 28 |
| Staphylococcus aureus | $1.13 \times 10^9$ | <10 | <10 | <10 | <10 |
| Escherichia coli | $4.16 \times 10^8$ | <10 | <10 | <10 | <10 |
| Pseudomonas aeruginosa | $8.0 \times 10^8$ | <10 | <10 | <10 | <10 |
| Candida albicans | $5.28 \times 10^7$ | <10 | <10 | <10 | <10 |
| Aspergillus niger | $5.5 \times 10^7$ | <10 | <10 | <10 | <10 |
| Burkholderia cepacia | $7.56 \times 10^8$ | <10 | <10 | <10 | <10 |

Table 4 includes the data related to anti-inflammatory and anti-oxidant activities of Bioactive Ingredient B. Anti-inflammatory activity was determined using human neutrophil elastase assay and anti-oxidant activity was determined using cytochrome c reduction assay.

TABLE 4

Anti-Inflammatory & Anti-Oxidant Activities of Bioactive Ingredient B

| Parameter | Results |
|---|---|
| Anti-Inflammatory Activity ($IC_{50}$), μl | 48.3 |
| Anti-Oxidant Activity ($IC_{50}$), μl | 7.5 |

Bioactive Ingredient B was determined to be stable (i.e., maintaining physical and chemical integrity) for at least 12 months while stored at a temperature of between 15 and 25° C. in a closed container protected from light.

Example 3

Characteristics and Properties of Bioactive Ingredient C

Bioactive Ingredient C was prepared according to the process described above in Example 1. Analyses of Bioactive Ingredient C were conducted to determine its various physico-chemical, chemical, microbial, and bioactivity characteristics.

The selected physico-chemical and chemical characteristics of Bioactive Ingredient C are presented below in Table 5.

TABLE 5

Physico-Chemical & Chemical Characteristics of Bioactive Ingredient C

| Parameter | Results |
|---|---|
| Appearance | Red-Brown Liquid |
| Odor | Characteristic |
| Color (Gardner Scale) | 18.5 |
| Dry Matter, % | 19.82 |
| Specific Gravity, g/cm$^3$ | 1.117 |
| Refractive Index, nD | 1.3770 |
| pH | 4.1 |
| UV Maximum, nm | 255 |
| Parthenolide, % | <0.00007 |

Bioactive Ingredient C is readily soluble in water in any proportion.

Table 6 below describes the microbial characteristics of Bioactive Ingredient C. This data demonstrates that Bioactive Ingredient C satisfies skin care industry requirements regarding total late count, mold and yeast count, and absence of pathogens.

TABLE 6

Microbial Characteristics of Bioactive Ingredient C

| Parameter | Results |
|---|---|
| Total Plate Count, CFU*/g | <100 |
| Mold &Yeast, CFU*/g | <10 |
| Escherichia coli | Negative |
| Salmonella sp. | Negative |
| Staphylococcus aureus | Negative |
| Pseudomonas sp. | Negative |

*Colony Forming Units

Table 7 relates to anti-inflammatory and anti-oxidant activities of Bioactive Ingredient C. Anti-inflammatory activity was determined using human neutrophil elastase assay and anti-oxidant activity was determined using cytochrome c reduction assay.

TABLE 7

Biological Activities of Bioactive Ingredient C

| Parameter | Results |
|---|---|
| Anti-Inflammatory Activity ($IC_{50}$), μl | 15.2 |
| Anti-Oxidant Activity ($IC_{50}$), μl | 3.1 |

Bioactive Ingredient C was determined to be stable (i.e., maintaining physical and chemical integrity) for at least 12 months while stored at a temperature of between 15 and 25° C. in a closed container protected from light.

Example 4

Characteristics and Properties of Bioactive Ingredient A

Bioactive Ingredient A was prepared according to the process described above in Example 1. Analyses of Bioactive Ingredient A were conducted to determine its various physico-chemical, chemical, microbial, and bioactivity characteristics.

The selected physico-chemical and chemical characteristics of Bioactive Ingredient A are presented below in Table 8.

TABLE 8

Physico-Chemical & Chemical Characteristics of Bioactive Ingredient A

| Parameter | Results |
|---|---|
| Appearance | Dark Beige Paste |
| Odor | Heavy Characteristic |
| Color (L* Value) | 27.83 |
| Color (a* Value) | 0.57 |
| Color (b* Value) | 8.24 |
| Dry Matter, % | 38.2 |
| Specific Gravity, g/cm$^3$ | 1.087 |
| pH | 9.0 |
| Parthenolide, % | 0.01 |

Table 9 below describes the microbial characteristics of Bioactive Ingredient A. This data demonstrates that Bioactive Ingredient A satisfies skin care industry requirements regarding total plate count, mold and yeast count, and absence of pathogens.

TABLE 9

Microbial Characteristics of Bioactive Ingredient A

| Parameter | Results |
|---|---|
| Total Plate Count, CFU*/g | <100 |
| Mold &Yeast, CFU*/g | <10 |
| Escherichia coli | Negative |
| Salmonella sp. | Negative |
| Staphylococcus aureus | Negative |
| Pseudomonas sp. | Negative |

*Colony Forming Units

Table 10 relates to anti-inflammatory and anti-oxidant activities of Bioactive Ingredient A. Anti-inflammatory activity was determined using human neutrophil elastase assay and anti-oxidant activity was determined using cytochrome c reduction assay.

TABLE 10

Biological Activities of Bioactive Ingredient A

| Parameter | Results |
|---|---|
| Anti-Inflammatory Activity ($IC_{50}$), μl | 11.2 |
| Anti-Oxidant Activity ($IC_{50}$), μl | 2.2 |

Bioactive Ingredient A was determined to be stable (i.e., maintaining physical and chemical integrity) for at least 12 months while stored in freezer in a closed container protected from light.

Example 5

Comparison of Bioactive Ingredients Obtained from Feverfew Collected from Different Harvests and in Different Seasons The reproducibility of Bioactive Ingredients was analyzed utilizing fresh feverfew which was harvested in two consecutive seasons from the same fields. Additionally fresh feverfew was harvested two times per season at the same stage of growth. All above fresh feverfew biomass samples were processed utilizing the method described above in Example 1. The data related to the comparison of the yield, selected characteristics and properties of Bioactive Ingredients B and C are presented below. (The data related to Bioactive Ingredient A are not included in the example, because this ingredient resulted in very small yield).

It was found, that from amount of feverfew to yield 100 kg dry matter approximately 12.4±2.1 kg of Bioactive Ingredients' dry matter were produced. The average dry matter in fresh feverfew biomass ~20% and thus ~190 kg of Bioactive Ingredient B or ~62 kg of Bioactive Ingredient C could be obtained.

No significant difference was found between yield of Bioactive Ingredients obtained from first and second harvest (p-value=0.8893) and between Bioactive Ingredients obtained in two consecutive seasons (p-value=0.6531). Additionally no significant difference was found between dry matter content in Bioactive Ingredients (p-value=0.5334) and parthenolide content in above ingredients (p-value=0.9923).

The selected physico-chemical and chemical characteristics of Bioactive Ingredients, which were obtained from fresh feverfew collected from different harvests and in different seasons, are presented below in Table 11 suggesting high reproducibility of Bioactive Ingredient B and Bioactive Ingredient C.

TABLE 11

Reproducibility of Bioactive Ingredients Obtained from Feverfew Collected from Different Harvests and in Different Seasons

| Parameter | Bioactive Ingredient B Mean ± StDev | Bioactive Ingredient C Mean ± StDev |
|---|---|---|
| Appearance | Yellow-Brown Liquid | Red-Brown Liquid |
| Odor | Characteristic | Characteristic |
| Color (Gardner Scale) | 10 ± 2 | ≥18 |
| Dry Matter, % | 6.6 ± 1.8 | 19.8 ± 2.3 |
| Specific Gravity, $g/cm^3$ | 1.035 ± 0.01 | 1.117 ± 0.02 |
| Refractive Index, nD | 1.3112 ± 0.004 | 1.3704 ± 0.01 |
| pH | 3.85 ± 0.4 | 3.95 ± 0.3 |
| UV Maximum, nm | 259 ± 3 | 256 ± 4 |
| Parthenolide, % | ≤0.00007 | ≤0.00007 |

It should be noted, that content of parthenolide in Bioactive Ingredients was below the detection limit of utilized HPLC analytical procedure.

Table 12 below describes the microbial characteristics of Bioactive Ingredients. This data demonstrates that Bioactive Ingredients obtained from feverfew collected from different harvests and in different seasons satisfy skin care industry requirements regarding total plate count, mold and yeast count, and absence of pathogens.

TABLE 12

Microbial Characteristics of Bioactive Ingredients Obtained from Feverfew Collected from Different Harvests and in Different Seasons

| Parameter | Bioactive Ingredient B | Bioactive Ingredient C |
|---|---|---|
| Total Plate Count, CFU*/g | <100 | <100 |
| Mold &Yeast, CFU*/g | <10 | <10 |
| Escherichia coli | Negative | Negative |
| Salmonella sp. | Negative | Negative |
| Staphylococcus aureus | Negative | Negative |
| Pseudomonas sp. | Negative | Negative |

*Colony Forming Units.

Table 13 relates to anti-inflammatory and anti-oxidant activities of Bioactive Ingredients. Anti-inflammatory activity was determined using human neutrophil elastase assay and anti-oxidant activity was determined using cytochrome c reduction assay. No significant difference was found between above activities of Bioactive Ingredients obtained from fresh feverfew collected from different harvests and in different seasons suggesting high reproducibility of Bioactive Ingredient B and Bioactive Ingredient C.

TABLE 13

Reproducibility of Biological Activities of Bioactive Ingredients Obtained from Feverfew Collected from Different Harvests and in Different Seasons

| Parameter | Bioactive Ingredient B Mean ± StDev | Bioactive Ingredient C Mean ± StDev |
|---|---|---|
| Anti-Inflammatory Activity ($IC_{50}$), μl | 48 ± 6 | 14 ± 3 |
| Anti-Oxidant Activity ($IC_{50}$), μl | 7.5 ± 2.4 | 3.1 ± 0.5 |

Bioactive Ingredients obtained from feverfew collected from different harvests and in different seasons were determined to be stable (i.e., maintaining physical and chemical integrity) for at least 12 months while stored in freezer in a closed container protected from light.

Example 6

Protocols Used for Determining Certain Characteristics of Bioactive Ingredients The following are various methods used for determining certain characteristics of Bioactive Ingredients. These methods are referenced throughout the above Examples. References below to the "tested products" or the "test samples" refer to Bioactive Ingredients.

Method for Determination of Dry Matter:

The procedure for determination of dry matter included evaporation of the tested product in the water bath at 100° C. until complete evaporation of water, oven storage of the sample at 105° C. for 3 hours, cooling to room temperature, and immediate determination of the weight of the container with solid matter.

Method for Determination of L*a*b* Values:

The procedure for determination of L*a*b* values utilized Hunter Labscan fixed geometry calorimeter with measuring geometry of 0°/45°. Standard illuminant $D_{65}$ with viewing window facing upward was used. The container with tested bioactive ingredient was placed on viewing window and measured through the bottom. The following CIELAB equations were used:

$$C^*=(a^{*2}+b^{*2})^{1/2}$$

$$DE^*=[(DL)^2+(Da^*)^2+(Db^*)^2]^{1/2}$$

$$DH=[(DE^*)^2-(DL^*)^2-(DC^*)^2]^{1/2}.$$

Method for Determination of Parthenolide Content:

The samples were extracted using methanol and 30 min ultrasonic treatment. The C18 reverse phase column was used as the stationary phase and 44% acetonitrile:56% water and 0.1% phosphoric acid was used as a mobile phase. Parthenolide detection was at 225 nm and parthenolide concentrations were determined using a multipoint calibration curve developed with six parthenolide standards (Sigma-Aldrich Corporation, St. Louis, Mo.) ranging from 30 μg/g to 900 μg/g. The detection limit under these conditions is 0.7 μg/ml. About 30 μg/g of parthenolide can be quantitated using these set of conditions.

Method for Determination of Microbiological Characteristics:

Microbiological characteristics of tested samples were determined in accordance with United States Pharmacopoeia (USP) method UPS XXVII, NF 22, <61>, Microbiological Limit Tests, which is hereby incorporated by reference in its entirety. The above tests include total aerobic count, total molds and yeast (aerobic plate count), determination of Salmonella (sp.), E. coli, Staphylococcus aureus and Pseudomonas sp.

Preservatives challenge studies were performed using method USP XXVII, NF 22, <51>, Antimicrobial Effective Testing, pp. 2148-2150, which is hereby incorporated by reference in its entirety. Incubation of the inoculated test articles was carried out at 20 to 25° C. and assayed at the time intervals of 7, 14, 21 and 28 days.

Method for Determination of Elastase Inhibitory Activity:

The elastase inhibitory activity of tested bioactive ingredients was determined using the assay, which employs human neutrophil elastase (Elastin Products Company, Inc., Owenswille, Mo.) and synthetic peptide soluble substrate N-MeO-Suc-Ala-Ala-Pro-Val-p-NA (Sigma-Aldrich Corporation, St. Louis, Mo.). This assay includes modified procedure as described in the Elastin Products Company's Catalog, "Determination of human elastase activity," Research Biochemical Catalog, Elastin Product Company, Inc., Owensville, Mo., at page 84 (2004), which is hereby incorporated by reference in its entirety. Enzymatic cleavage of the substrate was measured at 410 nm and 25° C. using 0.1 M Tris-HCl buffer pH 7.5 containing 50 mM NaCl. The total volume of reaction media in the spectrophotometer cuvette was 3.0 mL. Each tested bioactive ingredient was tested at concentrations required to achieve 50% inhibition ($IC_{50}$) of enzymatic reaction speed.

Method for Determination of Superoxide Scavenging Activity:

The method used was based on procedure described in the article Quick et al., "Rapid microplate assay for superoxide scavenging efficiency," J. Neuroscience Methods, 97:139-144 (2000), which is hereby incorporated by reference in its entirety.

This assay allowed for rapid and precise testing of bioactive ingredients to determine comparative antioxidant activity of superoxide scavenging. The assay included hypoxanthine, xanthine oxidase and cytochrome c. Hypoxanthine served as the substrate and was metabolized by xanthine oxidase in a two-step process, producing two superoxide anions. These free anions reduced cytochrome c, resulting in noticeable peak increase at 550 nm. The total volume of reaction media in the spectrophotometer cuvette was 3.0 mL.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A bioactive ingredient having anti-inflammatory activity comprising a cytoplasm fraction precipitate derived from cell juice of fresh biomass of a feverfew (Tanacetum parthenium) plant, wherein said cytoplasm fraction precipitate is produced by the process comprising:

providing fresh biomass of a feverfew (Tanacetum parthenium) plant;

processing the fresh biomass under conditions effective to yield a cell juice supernatant and a membrane fraction;

treating the cell juice supernatant under conditions effective to yield a first cell juice serum supernatant and a cytoplasm fraction precipitate; and isolating the cytoplasm fraction precipitate, wherein said cytoplasm fraction precipitate is a bioactive fraction that is substantially free of α-unsaturated γ-lactones, said α-unsaturated γ-lactones comprising parthenolide.

2. A bioactive ingredient having anti-inflammatory activity comprising a stabilized cell juice serum fraction derived from cell juice of fresh biomass of a feverfew (Tanacetum parthenium) plant, wherein said stabilized cell juice serum fraction is produced by a process comprising:

providing fresh biomass of a feverfew (Tanacetum parthenium) plant;

processing the fresh biomass under conditions effective to yield a cell juice supernatant and a membrane fraction;

treating the cell juice supernatant under conditions effective to yield a first cell juice serum supernatant and a cytoplasm fraction precipitate;

clarifying the first cell juice serum supernatant under conditions effective to yield a second cell juice serum supernatant; and mixing a stabilizing agent with the second cell juice serum supernatant under conditions effective to yield a stabilized cell juice serum fraction, wherein said stabilized cell juice serum fraction is a bioactive fraction that is *either free of α-unsaturated γ-lactones or* substantially free of α-unsaturated γ-lactones, said α-unsaturated γ-lactones comprising parthenolide.

3. The bioactive ingredient according to claim 2, wherein said stabilized cell juice serum fraction has an anti-inflammatory activity ranging from an $IC_{50}$ value of between about 0.01 percent (volume by volume) and about 2.0 percent (volume by volume), wherein said $IC_{50}$ value represents the concentration of bioactive ingredient required to decrease the speed of elastase enzymatic reaction by 50 percent.

4. The bioactive ingredient according to claim 2, wherein said stabilized cell juice serum fraction has an antioxidant activity ranging from an $IC_{50}$ value of between about 0.007 percent (volume by volume) and about 1.0 percent (volume by volume), wherein said $IC_{50}$ value represents the concentration of bioactive ingredient required to decrease the speed of cytochrome c reduction by 50 percent.

5. A bioactive ingredient having anti-inflammatory activity comprising a stabilized concentrated cell juice serum fraction derived from cell juice of fresh biomass of a feverfew (Tanacetum parthenium) plant, wherein said stabilized concentrated cell juice serum fraction is produced by a process comprising:

providing fresh biomass of a feverfew (Tanacetum parthenium) plant;

processing the fresh biomass under conditions effective to yield a cell juice supernatant and a membrane fraction;

treating the cell juice supernatant under conditions effective to yield a first cell juice serum supernatant and a cytoplasm fraction precipitate;

clarifying the first cell juice serum supernatant under conditions effective to yield a second cell juice serum supernatant;

mixing a stabilizing agent with the second cell juice serum supernatant under conditions effective to yield a stabilized cell juice serum fraction;

concentrating the stabilized cell juice serum fraction under conditions effective to yield a concentrated cell juice serum supernatant; and mixing a stabilizing agent with the concentrated cell juice serum supernatant under conditions effective to yield a stabilized concentrated cell juice serum fraction, wherein said stabilized concentrated cell juice serum fraction is a bioactive fraction that is free of α-unsaturated γ-lactones, said α-unsaturated γ-lactones comprising parthenolide.

6. The bioactive ingredient according to claim 5, wherein said stabilized concentrated cell juice serum fraction has an anti-inflammatory activity ranging from an $IC_{50}$ value of between about 0.01 percent (volume by volume) and about 2.0 percent (volume by volume), wherein said $IC_{50}$ value represents the concentration of bioactive ingredient required to decrease the speed of elastase enzymatic reaction by 50 percent.

7. The bioactive ingredient according to claim 5, wherein said stabilized concentrated cell juice serum fraction has an antioxidant activity ranging from an $IC_{50}$ value of between about 0.007 percent (volume by volume) and about 1.0 percent (volume by volume), wherein said $IC_{50}$ value represents the concentration of bioactive ingredient required to decrease the speed of cytochrome c reduction by 50 percent.

* * * * *